(12) United States Patent
Lubman et al.

(10) Patent No.: US 7,069,151 B2
(45) Date of Patent: Jun. 27, 2006

(54) MAPPING OF DIFFERENTIAL DISPLAY OF PROTEINS

(75) Inventors: David M. Lubman, Ann Arbor, MI (US); Bathsheba E. Chong, Paul, MN (US); Stephen J. Parus, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 631 days.

(21) Appl. No.: 09/778,496

(22) Filed: Feb. 7, 2001

(65) Prior Publication Data

US 2002/0039747 A1    Apr. 4, 2002

Related U.S. Application Data

(60) Provisional application No. 60/259,816, filed on Jan. 4, 2001, provisional application No. 60/259,448, filed on Jan. 3, 2001, provisional application No. 60/239,326, filed on Oct. 10, 2000, provisional application No. 60/239,325, filed on Oct. 10, 2000, provisional application No. 60/180,911, filed on Feb. 8, 2000.

(51) Int. Cl.
*G06F 19/00* (2006.01)
*C12M 1/34* (2006.01)

(52) U.S. Cl. .................... 702/19; 702/27; 435/288.6
(58) Field of Classification Search ............... 702/19; 435/173.1, 4
See application file for complete search history.

(56) References Cited

U.S. PATENT DOCUMENTS

| 5,498,545 A | 3/1996 | Vestal ................... 436/47 |
| 5,670,054 A | 9/1997 | Kibbey et al. ............ 210/656 |
| 6,534,764 B1 * | 3/2003 | Verentchikov et al. ...... 250/287 |

FOREIGN PATENT DOCUMENTS

| EP | 0617048 | 9/1994 |
| WO | WO9701755 | 1/1997 |
| WO | WO 98/40395 | 9/1998 |
| WO | WO0158925 | 8/2001 |
| WO | WO0158926 | 8/2001 |
| WO | WO02088701 | 7/2002 |

OTHER PUBLICATIONS

Chong, B.E., et al. Rapid Communications in Mass Spectrometry, 1998, vol. 12, pp. 1986-1993.*
Pandey et al. Proteomics to study genes and genomes. Nature. Jun. 15, 2000, vol. 405, pp. 837-846.*
Andrews, et al., Analysis of DNA adducts using high-performance seperation techniques coupled to electrosprayionization mass spectrometry, J Chromatogr A, 856 (1-2): 515 (1999).
Ball and Mascagni, Purification of synthetic peptides using reversible chromatographic probes based on the Fmoc molecule, Int J Pept Protein Res, 40(5):370 (1992).
Davidsson and Nilsson, Peptide mapping of proteins in cerebrospinal fluid utilizing a rapid preparative two-dimensional electrophoretic procedure and matrix-assisted laser desorption/ionization mass spectrometry, Biochim Biophys Acta, 1473(2-3):391 (1999).
Lee, Protein separation using non-porous sorbents, J Chromatogr B Biomed Sci Appl, 699(1-2):29 (1997).
Medzihradszky et al., Protein sequence and structural studies employing ionization-high energy collision-induced dissociation, International J of Mass Spectrometry and Ion Processes, 160(1):357 (1997).
Nimura et al., Fast Protein seperation by reversed-phase high-performance liquid chromatography on octadecylsilyl-bonded hon-porous silica gel effect of the particle efficiency, Journal of Liquid Chromatography, 585(2):207 (1991).
Richmond et al., High-throughput flow injection analysis-mass spectrometry with networked delivery of colour rendered results: the characterisation of liquid chromatography fractions, Journal of Chromatography, 835(1-2):29 (1999).
Patterson and Aebersold, Mass spectrometric approaches for the identification of gel-seperated proteins, Electrophoresis, 16(10):1791 (1995).
Wall, et al., Isoelectric focusing nonporous silica reversed-phase high-performance liquid chromatography/ electrospray ionization time-of-flight mass spectrometry: a three-dimensional liquid-phase protein seperation method as applied to the human erythroleukemia cell-line, rapid Commun Mass Spectrom, 15(18):1649 (2001).
Wall, et al., Three-dimensional protein map according to pl, hydrophobicity and molecular mass, J Chromatogr B Analyt Technol Biomed Life Sci, 774(1):53 (2002).

(Continued)

*Primary Examiner*—John S. Brusca
(74) *Attorney, Agent, or Firm*—Medlen & Carroll, LLP

(57) ABSTRACT

The present invention relates to protein separation systems and methods capable of resolving and characterizing large numbers of cellular proteins. In particular, the present invention provides a novel mass mapping system and methods for the differential display of proteins. The present invention further provides novel methods for displaying differential protein expression between two samples. In particular, the present invention provides novel method of mapping differential expression of proteins in non-cancerous, pre-cancerous, and cancerous cells.

35 Claims, 8 Drawing Sheets

OTHER PUBLICATIONS

Bini, et al., Protein expression profiles in human breast ductal carcinoma and histologically normal tissue, Electrophoresis, 18(15):2832 (197).

Chen, et al., Identification of proteins from two-dimensional gel electrophoresis of human erythroleukemia cells using capillary high performance liquid chromatography/electrospray-ion trap-reflectron time-of-flight mass spectrometry with two-dimensional topographic map analysis of in-gel tryptic digest products, Rapid Commun Mass Spectrom, 13 (19):1907 (1999).

Clauser, et al., Role of accurate mass measurement (+/− 10 ppm) in protein identification strategies employing MS or MS/MS and database searching, Anal chem, 71(14):2871 (1999).

Dai, et al., Two-layer sample preparation: a method for MALDI-MS analysis of complex peptide and protein mixtures, Anal Chem, 71(5):1087 (1999).

Damerval, Quantification od silver-stained proteins resolved by two-dimensional electrophoresis: genetic variability as related to abundance and solubility in two maize lines, Electrophoresis, 15(12):1573 (1994).

Fuqua, et al., Induction of the estrogen-regulated "24K" protein by heat shock, Cancer Res, 49(15):4126 (1989).

Herbert, Advances in protein solubilisation for two-dimensional electrophoresis, Electrophoresis, 20(4-5):660 (1999).

Hoogland C., The 1999 Swiss-2DPage database update., Nucleic Acids Res, 28:286 (2000).

Immler, et al., Identification of phosphorylated proteins from the thrombin-activated human platelets isolated by two-dimensional gel electrophoresis by electrospray ionization-tandem mass spectrometry (ESI-MS/MS) and liquid chromatography-electrospray ionization-mass spectrometry (LC-ESI-MS), Electrophoresis, 19(6):1015 (1998).

Kahn, From the genome to proteome: looking at al cell's proteins, Science, 270(5235):369 (1995).

Matsui, et al., Immobilized pH graident two-dimensional gel electrophoresis and mass spectrometric identification of cytokine-regulated proteins in ME-180 cervical carcinoma cells, Electrophoresis, 18(3-4):409 (1997).

Mohammad, et al., Induced expression of alpha-enolase in differentiated diffuse large cell lymphoma, Enzyme Protein, 48 (1):37 (1994).

Neidhardt, et al., Genomically linked cellular protein databases derived from two-dimensional polyacrylamide gel electrophoresis, Electrophoresis, 10(2):116 (1989).

Neubauer and Mann, Mapping of phosphorylation sites of gel-isolated proteins by nanoelectrospray tandem mass spectrometry: potentials and limitations, Anal Chem, 71(1):235 (1999).

O'Farrell, High resolution two-dimensional electrophoresis of proteins, J Biol Chem, 250(10):4007 (1975).

Opiteck, et al., Comprehensive two-dimensional high-performance liquid chromatography for the isolation of overexpressed proteins and proteome mapping, Anal Biochem, 258(2):349 (1998).

Patterson, Matrix-assisted laser-desorption/ionization mass spectrometric approaches for the identification of gel-separated proteins in the 5-50 pmol range, Electrophoresis, 16(7):1104 (1995).

Rasmussen, et al., Two-dimensional gel database of human breast carcinoma cell expressed proteins: an update, Electrophoresis, 19(5):818 (1998).

Redner, et al., The t(5;17) variant of acute promyelocytic leukemia expresses a nucleophosmin-retinoic acid receptor fusion, Blood, 87(3):882 (1996).

Rosenfeld, et al. In-gel digestion of proteins for internal sequence ananysis after one- or two-dimensional gel electrophoresis, Anal Biochem, 203(1):173 (1992).

Reymond, et al., Standardized charactedization of gene expression in human colorectal epithelium by two-dimensional electrophoresis, Electrophoresis, 18(15):2842 (1997).

Rosenfeld, et al. In-gel digestion of proteins for internal sequence ananysis after one- or two-dimensional gel electrophoresis, Anal Biochem, 203(1):173 (1992).

Sanchez, et al., Inside Swiss-2DPage database, Electrophoresis, 16(7):1131 (1995).

Sirover, New insights into an old protein: the functional diversity of mammalian glyceraldehyde-3-phosphate dehydrogenase, Biochim Biophys Acta, 1432(2):159 (1999).

Steller, Mechanisms and genes of cellular suicide, Science, 267(5203:1445 (1995).

Welsh, et al., Variation in expression of hsp27 messenger ribonucleic acid during the cycle of seminiferous epithelium and co-localization of hsp27 and microfilaments in Sertoli cells of the rat, Biol Reprod, 55(1):141 (1996); and.

Zugaro, et al., Characterization of rat brain stathmin isoforms by two-dimensional gel electrophoresis-matrix assisted laser desorption/ionization and electrospray ionization-ion trap mass spectrometry, Electrophoresis, 19(5):867 (1998).

Hermann and Andreas, Mapping and identification of Corynebacterium glutamicum proteins by two-dimensional gel electrophoresis and microsequencing, Electrophoresis, 19(18):3217 (1998) (abstract only).

Houen and Bach, Characterization of protein and carboxy-terminal ends using carboxypeptidease peptide Y: Sequence, composition, and identification of the carboxy-terminal peptide by peptide mapping, Methods Molecular Cellular Biology, 3(4):175 (1992) (abstract only).

Raznukov et al., Selective difital filtering of mass spectra of chromatography data for determination of "target" compounds in complex mixtures, Advances in Mass Spectrometry, 14(EO44280/I): (1998) (abstract only).

SZE and Dominic, Time-of-flight effects in matrix-assisted laser desorption/ionization Fourier transform mass spectrometry, Rapid Commun Mass Spectrom, 13(5):398 (1999) (abstract only).

Hanash, Advances in Electrophoresis, 1-44 (1998).

ten Hoeve, et al., Isolation and chromosomal localization of CRKL, a human crk-like gene, Oncogene, 8(9):2469 (1993).

Isobe et al., "Automated two-dimensional liquid chromatographic system for mapping proteins in highly complex mixtures," J. of Chromatography 588:115-123 (1991).

Opiteck et al., "Comprehensive On-Line LC/LDC/MS of Proteins, " Anal. Chem. 69:1524 (1997).

Carrier et al., "Using MultidimensionalMicroscale HPLC as an Alternative to 2D Page for Sample Preparation Prior to Nanole-MS/MS Protein Identification, " Poster Paper Presented at ASMS 2000.

Wagner et al., "Protein Mapping by two-Dimensaioral High Performance Liquid Chromatography," Journal of Chromatography A., 893:293-305 (2000).

* cited by examiner

FIG. 6A

| Peak | Acc. # | Protein Name | MW/pI | ESI-oaTOF |
|---|---|---|---|---|
| A | O43687 | A-KINASE ANCHOR PROTEIN 7 (A-KINASE ANCHOR PROTEIN 9 KDA) | 8968.9 / 4.95 | 8960 |
| B | P08708 | 40S RIBOSOMAL PROTEIN S17 | 15550.2 / 9.85 | 15520 |
| C | P33552 | CYCLIN-DEPENDENT KINASES REGULATORY SUBUNIT 2 (CKS-2) | 9860.4 / 8.07 | 9860 |
| D | P04792 | HEAT SHOCK 27 KDA PROTEIN (HSP 27) (STRESS-RESPONSIVE (ESTROGEN-REGULATED 24 KDA PROTEIN) (28 KDA HEAT SHOCK PROTEIN) | 22327.3 / 7.83 | 22620 |
| E | P28482 | MITOGEN-ACTIVATED PROTEIN KINASE 1 (EXTRACELLULAR MITOGEN-ACTIVATED SIGNAL-REGULATED KINASE 2) (ERK2) PROTEIN KINASE 2) (MAP KINASE 2) (MAPK 2) | 41389.9 / 6.50 | 41700 |
| F | P04155 | PS2 PROTEIN PRECURSOR (HP1.A) (BREAST CANCER ESTROGEN-INDUCIBLE PROTEIN) (PNR-2) | 9149.6 / 4.29 (unprocessed precursor) | 8960 |
| G | P01116 | TRANSFORMING PROTEIN P21/K-RAS 2A | 21656.0 / 6.33 | 21700 |
|  | P01236 | PROLACTIN PRECURSOR (PRL) | 25876.0 / 6.50 | 25920 |
| H | P11766 | ALCOHOL DEHYDROGENASE CLASS III CHI CHAIN | 39724.5 / 7.45 | 39575 |
|  | Q07002 | SERINE/THREONINE PROTEIN KINASE PCTAIRE-3 | 43359.4 / 9.02 | 44330 |
| I | P10159 | INITIATION FACTOR 5A (EIF-5A) (EIF-4D) (REV BINDING FACTOR | 16832.4 / 5.08 | 16830 |

| | | | |
|---|---|---|---|
| | P03996 | ACTIN | 42009.2 / 5.24 | 42010 |
| | P01106 | MYC PROTO-ONCOGENE PROTEIN (C-MYC) | 48804.3 / 5.33 | 48840 |
| J | P56937 | ESTRADIOL 17 BETA-DEHYDROGENASE 7 (17-BETA-HSD 7) (17-BETA-HYDROXYSTEROID DEHYDROGENASE 7) | 38206.4 / 8.35 | 38220 |
| K | Q00987 | UBIQUITIN-PROTEIN LIGASE E3 MDM2 (P53-BINDING PROTEIN MDM2) (ONCOPROTEIN MDM2) | 55233.2 / 4.60 | 55220 |
| L | P08758 | ANNEXIN V | 35936.9 / 4.94 | 35890 |
| | P08779 | (CYTOKERATIN 17) (K17) (CK 17) (VERSI | 50699.4 / 4.97 | 50470 |
| M | Q9Y2U5 | MITOGEN-ACTIVATED PROTEIN KINASE KINASE KINASE 2 (MAPK/ERK KINASE KINASE 2) (MEK KINASE 2) (MEKK 2) | 69538.0 / 8.47 | 69670 |
| N | P04637 | CELLULAR TUMOR ANTIGEN P53 (PHOSPHOPROTEIN P53) | 43653.4 / 6.33 | 46280 |
| O | P54652 | HEAT SHOCK-RELATED 70 KD PROTEIN 2 (HEAT SHOCK 70 KD PROTEIN 2) | 70021.3 / 5.56 | 70030 |
| P | P11474 | STEROID HORMONE RECEPTOR ERR1 (ESTROGEN-RELATED RECEPTOR, ALPHA) (ERR-ALPHA) (ESTROGEN RECEPTOR-LIKE 1) | 55439.9 / 6.28 | 55450 |
| Q | P12931 | PROTO-ONCOGENE TYROSINE-PROTEIN KINASE SRC (P60-SRC) (C-SRC) | 59835.1 / 7.11 | 60540 |

FIG. 6B

MAPPING OF DIFFERENTIAL DISPLAY OF PROTEINS

This appln. claims priority benefit of U.S. Provisional application Ser. Nos. 60/180,911, filed Feb. 8, 2000, 60/239,325, filed Oct. 10, 2000, filed Oct. 10, 2000, 60/259,448, filed Jan. 3, 2001, and 60/259,816 filed Jan. 1, 2001, each of which is herein incorporated by reference in their entireties.

The present invention was made, in part, with government funding under National Institutes of Health under grant No. 2-R01GM49500-5 and the National Science Foundation grant No. DBI-9987220. The government has certain rights in this invention.

FIELD OF THE INVENTION

The present invention relates to protein separation systems and methods capable of resolving and characterizing large numbers of cellular proteins. In particular, the present invention provides novel mass mapping systems and methods for the differential display of proteins.

BACKGROUND OF THE INVENTION

As the nucleic acid sequences of a number of genomes, including the human genome, become available, there is an increasing need to interpret this wealth of information. While the availability of nucleic acid sequence information allows for the prediction and identification of genes, it does not explain the expression patterns of the proteins produced from these genes. The genome does not describe the dynamic processes on the protein level. For example, the identity of genes and the level of gene expression does not represent the amount of active protein in a cell nor does the gene sequence describe post-translational modifications that are essential for the function and activity of proteins. Thus, in parallel with the genome projects there has begun an attempt to understand the proteome (i.e., the quantitative protein expression pattern of a genome under defined conditions) of various cells, tissues, and species. Proteome research seeks to identify targets for drug discovery and development and provide information for diagnostics (e.g., tumor markers).

An important aspect of genome and proteome analysis is the ability to differentiate expression patterns between two related samples (e.g., differentiated and undifferentiated cells, cancer cells and normal cells, drug-treated cells and untreated cells, etc.). The importance of such techniques can be seen by looking at the example of cancer cells. An important current area of research involves developing an understanding of the mechanisms behind cancer progression. In order to follow changes in cancer cells at the molecular level, methods are used that monitor the activation of different genes as the cancer process evolves. This is usually performed by monitoring mRNA expression using techniques such as differential display (Liang and Pardee, Science 257:967 [1992] and Miller et al., Electrophoresis 20:256 [1999]) and subtractive hybridization (Schweinfest and Papas, Intern. J. Oncol., 1:499 [1992]). The differential display method is based upon the systematic amplification of portions of mRNAs, which are then resolved on a DNA sequencing gel. On the other hand, the subtractive hybridization method works by subtracting cDNAs reverse transcribed from mRNA from two physiological states. This allows for the isolation of transcripts that are differentially expressed. The isolated transcripts then undergo a series of hybridization reactions followed by selective amplification.

Even though these methods provide information on gene activation, there are inherent problems with them (Sturtevant, Clin. Micro. Rev., 13:408 [2000]). Since the methodology depends upon amplification of rare transcripts by PCR, results are semi-quantitative at best, where the ability to study quantitative changes is often important. Also, bands that are differentially displayed in one trial are often difficult to reproduce in a second run and differential expression is often difficult to confirm by Northern blotting. However, often the mRNA is altered without a corresponding change observed in protein levels, and protein levels are frequently altered without a corresponding change observed in mRNA levels (Russel et al., Oncogene 18:1983 [1999] and Ozturk et al., Anal. Cell Pathol. 16:201 [1998]).

The problems involved with correlating changes in cancer cells to mRNA expression have led investigators to study altered protein expression in cancer progression. Since proteins are the basic entities that perform functions in the cells, it becomes logical to follow changes in protein expression as cells progress to malignancy. This involves using methods to monitor changes in quantitative expression of proteins and also structural changes in proteins during progression. The classic methods for following such changes in protein expression involve 1-D and 2-D polyacrylamide-gel electrophoresis. The 1-D gel method is generally a simple method used to achieve a crude separation of cell lysates where the most abundant proteins can be separated and detected. Although a relatively low resolution technique, 1-D gel method remains a general method for monitoring the more highly expressed proteins in cells. 2-D gel electrophoresis is a high resolution method capable of separating out hundreds of protein spots, where the spot pattern is characteristic of the cell protein expression. 2-D gel patterns have been traditionally used to study changes in proteins that are peculiar to stages of cancer progression (Lopez, Electrophoresis 21:1082 [2000]; Langen, Electrophoresis 21:2105 [2000]; and Williams et al., Electrophoresis 19:333 [1998]).

Gel electrophoresis methods (1-D and 2-D) have certain fundamental limitations for screening and identification of proteins from cells. Gel electrophoresis separations are slow, where even a 1-D gel requires nearly eight hours to run with bands having sufficient resolution to study protein changes. Also, gel electrophoresis only provides separation, where for proteins that change in expression, identification of the proteins is required. Although various procedures have been developed for identifying proteins based upon MALDI-MS of in-gel digests (Shevchenko et al., Anal. Chem., 68:850 [1996]; Courchesne et al., Electrophoresis 18:369 [1997]; Aebersold et al., Proc. Natl. Acad. Sci. USA 84:6970 [1987]; Waltham et al., Electrophoresis 18:391 [1997]; and Henzel et al., Proc. Natl. Acad. Sci., USA 90:5011 [1993]), the procedures remain rather labor intensive and laborious. In addition, direct determination of the molecular weight of intact proteins from gels remains difficult, although there have been several new developments for molecular weight determination (Loo et al., Anal. Chem., 68:1910 [1996]; Cohen and Chait, Anal. Biochem., 247:257 [1997] and Liang et al., Anal. Chem., 68:1012 [1996]). Another significant problem with gel electrophoresis is quantitation, where small changes in expression (plus or minus 10%) are often difficult to observe with Coomassie staining, and quantitation at any level is difficult with silver staining (Rodriguez et al, Electrophoresis 14:628 [1993]). Other methods are required to routinely screen for changes in protein expression and identification. Thus, what is needed are new methods and systems to allow efficient and informative comparison of protein expression patterns between cells (e.g., cancer and normal cells).

SUMMARY OF THE INVENTION

The present invention relates to protein separation systems and methods capable of resolving and characterizing large numbers of cellular proteins. In particular, the present invention provides a novel mass mapping system and methods for the differential display of proteins.

The present invention provides a method, comprising: providing: i) a first sample comprising a plurality of proteins; ii) a second sample comprising a plurality of proteins; iii) a separating apparatus, wherein the separating apparatus is capable of separating proteins based on a physical property; iv) a mass spectroscopy apparatus; and treating the first and second samples with the separating apparatus to produce a first separated protein sample and a second separated protein sample, wherein the first and second separated protein samples are collected from the separating apparatus in a plurality of fractions, each of the fractions defined by a physical property; and analyzing the plurality of fractions from each of the first and second separated protein samples with the mass spectroscopy apparatus to produce a protein profile map for each of the first and second samples.

In some embodiments, the methods of the present invention further include an automated sample handling device operably linked to the separating apparatus and the mass spectroscopy apparatus, wherein the sample handling device transfers the first and second samples to the separating apparatus, and wherein the sample handling device transfers the first and second separated protein samples from the separating apparatus to the mass spectroscopy apparatus. In some embodiments, the methods of the present invention further comprise a centralized control network operably linked to the automated sample handling device, the separating apparatus, and the mass spectroscopy apparatus, wherein the centralized control network controls the operations of the automated sample handling device, the separating apparatus, and the mass spectroscopy apparatus. In some embodiments, the centralized control network comprises computer memory and a computer processor.

In some embodiments, the first sample comprises a cell lysate from a first cell type and the second sample comprises a cell lysate from second cell type. In some embodiments, the first cell type is a cancerous cell type and the second cell type is a non-cancerous cell type. In some embodiments, additional samples (e.g., third, fourth, fifth, etc.) are included. In some embodiments, the additional samples comprise cell lysates from additional cell types (e.g., including but not limited to, pre-cancerous cells and cells from different stages of a cancer). In other embodiments, the additional samples comprise cell lysates from the same cell types that have each been treated with a different external agent (e.g., pharmacological agent or environmental toxin).

In some embodiments, the protein profile map displays a comparison of protein abundance and mass between the first protein sample and the second protein sample. In some embodiments, the protein profile map displays a comparison of the additional samples (e.g., third, fourth, fifth, etc.). In some embodiments, protein abundance is expressed as bands of varying intensity or different colors. In preferred embodiments, protein abundance and mass are indicative of the cell type of the protein sample. In some preferred embodiments, the protein profile map distinguishes between post-translational modifications of the same protein (e.g., including, but not limited to, truncations, glycosylation, and phosphorylation). In some preferred embodiments, the methods of the present invention further comprise determining the identity of individual bands on the protein profile map. In some embodiments, the first sample is treated with an external agent (e.g., a drug or an environmental toxin) prior to treating the first and second samples with the separating apparatus. In some embodiments, the external agent is estradiol.

In some embodiments, the automated sample handling device comprises a switchable, multi-channel valve. In some embodiments, the first and second samples further comprises a buffer, wherein the plurality of proteins are solubilized in the buffer and wherein the buffer is compatible with the separating apparatus and the mass spectroscopy apparatus. In some embodiments, the buffer comprises a compound of the formula n-octyl SUGARpyranoside (e.g., n-octyl $C_6$–$C_{12}$ glycopyranoside, where $C_6$-$C_{12}$ glycopyranoside is a six to twelve carbon sugar pyranoside). The present invention is not limited to any one buffer of the formula n-octyl SUGARpyranoside. Indeed, a variety of formulations are contemplated, including but not limited to, n-octyl β-D-glucopyranoside and n-octyl β-D-galactopyranoside. In some preferred embodiments, the separating apparatus comprises a liquid phase separating apparatus. In some embodiments, the liquid phase separating apparatus comprises a reverse phase HPLC separating apparatus. In preferred embodiments, the reverse phase HPLC comprises non-porous reverse phase HPLC.

In some embodiments, prior to said analyzing the first and second separated protein samples by mass spectroscopy, the samples are divided into first and second portions and the second portions are subjected to enzymatic digestion. In some embodiments, analyzing the first and second separated protein samples by mass spectrometry comprises analyzing the samples by ESI oa TOF/MS. The present invention is not limited to any one mass spectroscopy technique. Indeed, a variety of techniques are contemplated, including but not limited to, ion trap mass spectrometry, ion trap/time-of-flight mass spectrometry, quadrupole and triple quadrupole mass spectrometry, Fourier Transform (ICR) mass spectrometry, and magnetic sector mass spectrometry.

The present invention also provides a method, comprising providing: i) a cell lysate derived from a cell of unknown type, the cell lysate comprising a plurality of proteins; ii) a first protein profile map (e.g., generated by the methods of the present invention); iii) a separating apparatus, wherein the separating apparatus is capable of separating proteins based on a physical property; and iv) a mass spectroscopy apparatus; and treating the cell lysate with the separating apparatus to produce a separated protein sample; wherein the separated protein sample is collected from the separating apparatus in a plurality of fractions, each of the fractions defined by a physical property; analyzing the plurality of fractions from the separated protein samples with the mass spectroscopy apparatus to produce a second protein profile map; and comparing the first protein profile map and the second protein profile map.

In some embodiments, the first protein profile map displays protein abundance and mass from cell lysates of several known cell types and the second protein profile map displays protein abundance and mass from said cell lysate of unknown type. In some embodiments, the known cell types are non-cancerous, pre-cancerous, and cancerous cell types. In some embodiments, the protein abundance is expressed as bands of varying intensity or of different colors. In some embodiments, the protein abundance and mass are indicative of the cell type of the protein sample. In some preferred embodiments, the protein profile map distinguishes between post-translational modifications of the same protein.

The present invention further provides a system comprising: a reverse phase HPLC separating apparatus; an automated sample handling apparatus configured to receive separated proteins from the reverse phase HPLC separating apparatus; and a mass spectroscopy apparatus configured to receive proteins from the automated sample handling apparatus; a processor, wherein the processor is capable of producing a protein profile map of separated proteins analyzed by the mass spectroscopy apparatus; and a display apparatus capable of displaying the protein profile map.

In some embodiments, the protein profile map displays a comparison of protein abundance and mass between the first protein sample and the second protein sample. In some embodiments, the protein abundance is expressed as bands of varying intensity. In some preferred embodiments, the protein abundance is expressed as bands of different colors. In some embodiments, the protein abundance and mass are indicative of the cell type of the protein sample. In some preferred embodiments, the processor is capable of determining the identity of individual bands on the protein profile map.

In some embodiments, the automated sample handling device comprises a switchable, multi-channel valve. In some embodiments, the mass spectrometry apparatus comprises a ESI oa TOF/MS apparatus. The present invention is not limited to any one mass spectroscopy technique. Indeed, a variety of techniques are contemplated, including but not limited to, ion trap mass spectrometry, ion trap/time-of-flight mass spectrometry, quadrupole and triple quadrupole mass spectrometry, Fourier Transform (ICR) mass spectrometry, and magnetic sector mass spectrometry.

DESCRIPTION OF THE FIGURES

FIG. 6 shows the identity and molecular weight of proteins identified from tryptic peptide maps using PDE-MALDI-TOF MS for AT1E lysates.

GENERAL DESCRIPTION OF THE INVENTION

Figure 1:
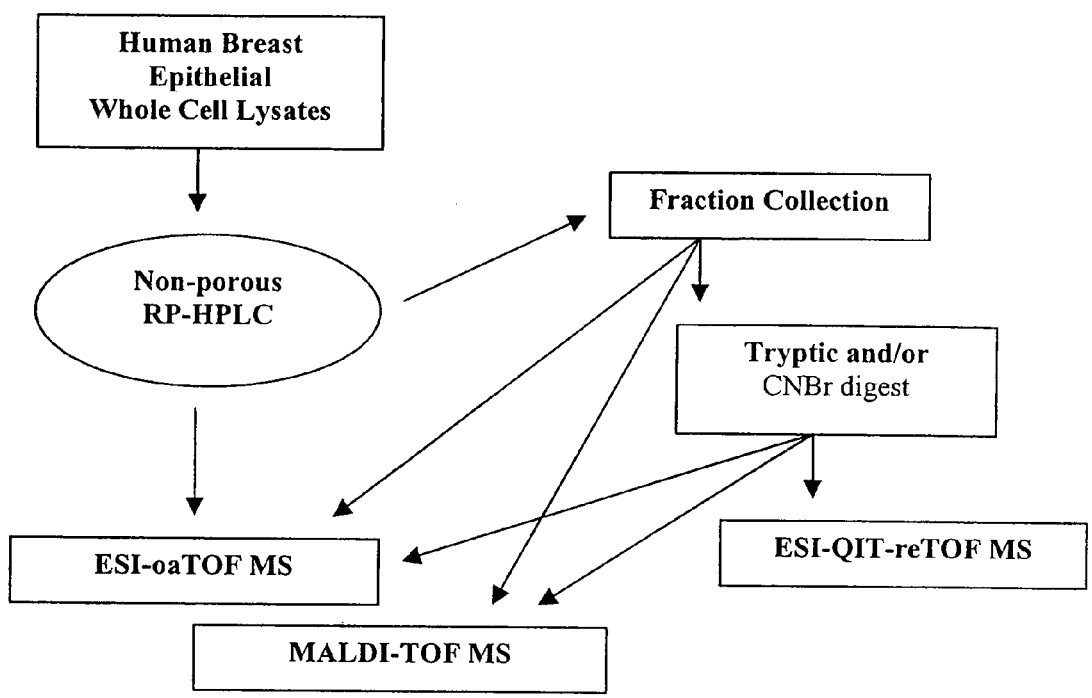
FIG. 1 shows an overview of the methodology of multidimensional non-porous LC-MS protein analysis methods used in some embodiments of the present invention.

The present invention relates to protein separation systems and methods capable of resolving large numbers of cellular proteins. The methods of the present invention provide protein profile maps for imaging and comparing protein expression patterns. The present invention provides alternatives to traditional separation methods for the screening of protein profiles. For example, in some embodiments of the present invention, non-porous reverse-phase HPLC is used to separate and analyze proteins as an alternative to 1-D gels. Such methods are described herein, demonstrating their effectiveness for comparing expression profiles between cells.

For example, data produced using the systems and methods of the present invention has provided accurate and informative expression information from whole cell lysates of human breast cancer cell lines. A series of cell lines representing sequential stages in the development of breast cancer (MCF10 model) were examined. These cell lines have been developed from spontaneously immortalized breast epithelial cells obtained from a patient with fibrocystic disease (Soule et al., Cancer Research 50:6075 [1990]) and include premalignant (Miller et al., J. Natl. Cancer Inst., 85:1725 [1993]) and Dawson et al, Am. J. Pathol., 148:313 [1996]) as well as malignant cell lines (Santner et al., Proc. Am. Assoc. Cancer Res., 39:202 [1998]). As all stages are derived from a single patient, differences in background gene expression are minimized. Using the systems and methods of the present invention, it was shown that elevated levels of proteins or the appearance of new proteins can be observed in malignant cells as compared to premalignant or normal cells. Moreover, a mass map of intact proteins from cell lysates can be obtained. This mass map can be used for differential display of protein molecular weights in order to observe differences in quantitative expression and changes in structure due to post translational modifications. In addition, proteins can be collected in the liquid phase and identified by mass spectroscopy tryptic mapping procedures. Of great relevance, it is shown that distinct changes in phosphorylation patterns are observed during neoplastic progression.

The systems and methods of the present invention may be used to analyze any protein-containing sample and to compare the protein content of the sample to other desired samples (e.g., sample from another cell or reference sample that represent a known condition or status). A major advantage of the systems and methods of the present invention over traditional techniques is the rapid assay times and amenability to automation. For example, in some preferred embodiments of the present invention, proteins are processed in the liquid phase to allow automated transfer of the analyzed sample from one apparatus (e.g., a separation column) to another apparatus (e.g., mass spectrometer). In recent work, several liquid phase based techniques have been developed for separation of proteins (Yang et al., Anal. Chem., 70:3235 [1998]; Opitek et al., Anal. Biochem., 258:344 [1998]; Ayala et al, Appl. Biochem. Biotech., 69:11 [1998]; Hayakawa et al., Anal. Chim. Acta 372:281 [1998]; Nilsson et al., Electrophoresis 20:860 [1999]; Nilsson et al., Rapid Comm. Mass Spec., 11:610 [1997]; Davidsson et al., Anal. Chem., 71:642 [1999]). Of note has been the use of a nonporous (NP) silica based media for separation of proteins in reversed-phase HPLC. This media has been used for separation of proteins from whole cell lysates of bacterial cells and various mammalian cells (Wall et al., Anal. Chem., 71:3894 [1999] and Chong et al., Rapid Commun. Mass Spec., 13:1808 [1999]). These NP packing materials have been shown to provide important advantages in the separation of protein mixtures where separations of whole cell lysates can be performed in 15–30 minutes with excellent resolution. The use of these NP materials in reverse phase HPLC avoids the problems of proteins sticking inside the pores of the porous materials and results in considerably improved resolution and protein recovery. Of great importance is that the ability to separate and isolate proteins in the liquid phase allows easy interfacing of the separation methods to mass detection techniques for identification and molecular weight analysis.

Definitions

To facilitate an understanding of the present invention, a number of terms and phrases are defined below:

As used herein, the term "multiphase protein separation" refers to protein separation comprising at least two separation steps. In some embodiments, multiphase protein separation refers to two or more separation steps that separate proteins based on different physical properties of the protein (e.g., a first step that separates based on protein charge and a second step that separates based on protein hydrophobicity).

As used herein, the term "protein profile maps" refers to representations of the protein content of a sample. For example, "protein profile map" includes 1-dimensional displays of total protein expressed in a given cell. In some embodiments, protein profile maps may also display subsets of total protein in a cell. Protein profile maps may be used for comparing "protein expression patterns" (e.g., the amount and identity of proteins expressed in a sample) between two or more samples. Such comparing find use, for example, in identifying proteins that are present in one sample (e.g., a cancer cell) and not in another (e.g., normal tissue), or are over- or under-expressed in one sample compared to the other.

As used herein, the term "separating apparatus capable of separating proteins based on a physical property" refers to compositions or systems capable of separating proteins (e.g., at least one protein) from one another based on differences in a physical property between proteins present in a sample containing two or more protein species. For example, a variety of protein separation columns and composition are contemplated including, but not limited to ion exclusion, ion exchange, normal/reversed phase partition, size exclusion, ligand exchange, liquid/gel phase isoelectric focusing, and adsorption chromatography. These and other apparatuses are capable of separating proteins from one another based on a "physical property." Examples of physical properties include, but are not limited to, size, charge, hydrophobicity, and ligand binding affinity. Such separation techniques yield fractions or subgroups of proteins "defined by a physical property," i.e., separated from other proteins in the sample on the basis of a difference in a physical property, but with all of the proteins in the fraction or subgroup sharing that physical property. For example, all of the proteins in a fraction may elute from a column at a defined solution condition (e.g., salt concentration) or narrow range of solution conditions, while other proteins not in the fraction remain bound to the column or elute at different solution conditions.

A "liquid phase" separating apparatus is a separating apparatus that utilizes protein samples contained in liquid solution, wherein proteins remain solubilized in liquid phase during separation and wherein the product (e.g., fractions) collected from the apparatus are in the liquid phase. This is in contrast to gel electrophoresis apparatuses, wherein the proteins enter into a gel phase during separation. Liquid phase proteins are much more amenable to recovery/extraction of proteins as compared to gel phase. In some embodiments, liquid phase proteins samples may be used in multi-step (e.g., multiple separation and characterization steps) processes without the need to alter the sample prior to treatment in each subsequent step (e.g., without the need for recovery/extraction and resolubilization of proteins).

As used herein, the term "displaying proteins" refers to a variety of techniques used to interpret the presence of proteins within a protein sample. Displaying includes, but is not limited to, visualizing proteins on a computer display representation, diagram, autoradiographic film, list, table, chart, etc. "Displaying proteins under conditions that first and second physical properties are revealed" refers to displaying proteins (e.g., proteins, or a subset of proteins obtained from a separating apparatus) such that at least two different physical properties of each displayed protein are revealed or detectable. For example, such displays include, but are not limited to, tables including columns describing (e.g., quantitating) the first and second physical property of each protein and two-dimensional displays where each protein is represented by an X,Y locations where the X and Y coordinates are defined by the first and second physical properties, respectively, or vice versa. Such displays also include multi-dimensional displays (e.g., three dimensional displays) that include additional physical properties.

As used herein, the term "detection system capable of detecting proteins" refers to any detection apparatus, assay, or system that detects proteins derived from a protein separating apparatus (e.g., proteins in one or fractions collected from a separating apparatus). Such detection systems may detect properties of the protein itself (e.g., UV spectroscopy) or may detect labels (e.g., fluorescent labels) or other detectable signals associated with the protein. The detection system converts the detected criteria (e.g., absorbance, fluorescence, luminescence etc.) of the protein into a signal that can be processed or stored electronically or through similar means (e.g., detected through the use of a photomultiplier tube or similar system).

As used herein, the term "buffer compatible with an apparatus" and "buffer compatible with mass spectrometry" refer to buffers that are suitable for use in such apparatuses (e.g., protein separation apparatuses) and techniques. A buffer is suitable where the reaction that occurs in the presence of the buffer produces a result consistent with the intended purpose of the apparatus or method. For example, a buffer compatible with a protein separation apparatus solubilizes the protein and allows proteins to be separated and collected from the apparatus. A buffer compatible with mass spectrometry is a buffer that solubilizes the protein or protein fragment and allows for the detection of ions following mass spectrometry. A suitable buffer does not substantially interfere with the apparatus or method so as to prevent its intended purpose and result (i.e., some interference may be allowed, but not enough to prevent an accurate determination of mass).

As used herein, the term "automated sample handling device" refers to any device capable of transporting a sample (e.g., a separated or un-separated protein sample) between components (e.g., separating apparatus) of an automated method or system (e.g., an automated protein characterization system). An automated sample handling device may comprise physical means for transporting sample (e.g., multiple lines of tubing connected to a multi-channel valve). In some embodiments, an automated sample handling device is connected to a centralized control network.

As used herein, the term "switchable multi channel valve" refers to a valve that directs the flow of liquid through an automated sample handling device. The valve preferably has a plurality of channels (e.g., 4 or more, and preferably, 6 or more). In addition, in some embodiments, flow to individual channels is "switched" on an off. In some embodiments, valve switching is controlled by a centralized control system. A switchable multi-channel valve allows multiple apparatus to be connected to one automated sample handler. For example, sample can first be directed through one apparatus of a system (e.g., a first chromatography apparatus). The sample can then be directed through a different channel of the valve to a second apparatus (e.g., a second chromatography apparatus).

As used herein, the terms "centralized control system" or "centralized control network" refer to information and equipment management systems (e.g., a computer processor and computer memory) operably linked to multiple devices or apparatus (e.g., automated sample handling devices and separating apparatus). In preferred embodiments, the centralized control network is configured to control the operations of the apparatus and device linked to the network. For example, in some embodiments, the centralized control network controls the operation of multiple chromatography apparatus, the transfer of sample between the apparatus, and the analysis and presentation of data.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refers to a device that is able to read a program from a computer memory (e.g., ROM or other computer memory) and perform a set of steps according to the program.

As used herein, the term "sample" is used in its broadest sense. In one sense it can refer to a cell lysate. In another sense, it is meant to include a specimen or culture obtained from any source, including biological and environmental samples. Biological samples may be obtained from animals (including humans) and encompass fluids, solids, tissues, and gases. Biological samples include blood products (e.g., plasma and serum), saliva, urine, and the like and includes substances from plants and microorganisms. Environmental samples include environmental material such as surface matter, soil, water, and industrial samples. These examples are not to be construed as limiting the sample types applicable to the present invention.

DETAILED DESCRIPTION OF THE INVENTION

The present invention provides a novel separation methods for the detection of differential expression of proteins in two or more cell types (e.g., in cancerous and non-cancerous cell lines). The present invention is not limited by the type of samples being compared. The methods of the present invention are suitable for use in any situation where it is advantageous to determine the difference in protein expression between two or more samples. The present invention thus provides methods suitable for a variety of diagnostic, screening (e.g., drug screening), and research uses, including, but not limited to, those disclosed herein.

In some preferred embodiments, the present invention provides methods of separating proteins using any suitable protein separation technique (e.g., non-porous RP-HPLC) linked to mass spectroscopy to generate a protein mass map, and comparing expression patterns among one or more samples. The following discussion is provided in two sections: I) separation and mass spectroscopic analysis; and II) differential protein expression in human breast cancer cell lines.

I. Separation and Analysis

In some embodiments, the present invention provides methods of separating and analyzing protein expression in one or more cell lines or types. Cells are lysed using any suitable method, including but not limited to, those disclosed herein. Following lysis, cell extracts are first separated based on a physical property. The present invention is not limited to separation based on any particular property. Nor is the present invention limited to any particular separation method.

Following separation, the mass, abundance, and identity of proteins in the different cell samples being analyzed is determined (e.g., using mass spectroscopy). The present invention in not limited to any particular detection or mass spectroscopy technique. Any suitable mass spectroscopy technique may be utilized, including but not limited to, those disclosed herein. In some embodiments, following mass spectroscopy, a 1-D protein map is generated that compares the protein expression levels of the various samples being analyzed.

In some embodiments of the present invention, protein separation and analysis is automated. In some embodiments, the process is controlled by a centralized control network including an automated sample handling device and a centralized control network.

A. Separation

In preferred embodiments, prior to analyzing protein mass and expression patterns, proteins are separated based on one or more physical properties. For example, in some embodiments of the present invention, proteins are separated by hydrophobicity using non-porous (NP) reversed phase (RP) HPLC (See e.g., Liang et al., Rap. Comm. Mass Spec., 10:1219 [1996]; Griffin et al., Rap. Comm. Mass Spec., 9:1546 [1995]; Opiteck et al., Anal. Biochem. 258:344 [1998]; Nilsson et al., Rap. Comm. Mass Spec., 11:610 [1997]; Chen et al., Rap. Comm. Mass Spec., 12:1994 [1998]; Wall et al., Anal. Chem., 71:3894 [1999]; Chong et al, Rap. Comm. Mass Spec., 13:1808 [1999]). Illustrative Example 2 provides a description of one NP-HPLC method suitable for use in the present invention. One skilled in the art recognizes that other NP-HPLC or separation methods may be utilized in the methods of the present invention.

The present invention provides the novel combination of employing non-porous RP packing materials (Eichrom) with a RP HPLC compatible detergent (e.g., n-octyl β-D-galactopyranoside) to facilitate the separation and mass detection methods of the present invention. This detergent is also compatible with mass spectrometry due to its low molecular weight. These columns are well suited to this task as the non-porous packing they contain provides optimal protein recovery and rapid efficient separations. It should be noted that though several detergents are disclosed herein for increasing protein solubility while being compatible with RP HPLC there are many other different detergents (e.g., low molecular weight non-ionic) that could be used for this purpose.

This method provides for exceptionally fast and reproducible high-resolution separations of proteins according to their hydrophobicity and molecular weight. The non-porous silica packing material used in these reverse phase separations eliminates problems associated with porosity and low recovery of larger proteins, as well as reducing analysis times by as much as one third. Separation efficiency remains high due to the small diameter of the spherical particles, as does the loadability of the NP RP HPLC columns.

In some embodiments, proteins are reduced and alkylated (e.g., with DTE and iodoacetamide respectively) prior to the NP-HPLC step. This step insures that all disulfide bonds are broken and optimal proteolysis is produced. This derivatization step can be added to the NP RP HPLC method by performing the reduction and alkylation step prior to NP RP HPLC or during cell lysis.

The present invention is not limited to any one separation technique. Indeed, a variety of separation techniques are contemplated, including, but not limited to, 1-D SDS PAGE lane gels and various chromatography techniques.

In some preferred embodiments, the separation is performed in the liquid phase. Separation in the liquid phase facilitates efficient analysis of the separated proteins and enables products to be fed directly into additional analysis steps (e.g., directly into mass spectrometry analysis). In some preferred embodiments involving separation in the liquid phase, sample handling is automated. For example, an automated sample handler is utilized to transfer samples to the HPLC apparatus, collect peak fractions, and transfer fractions to the mass spectroscopy analysis step.

B. Mass Spectroscopy Analysis

In preferred embodiments of the present invention, separation (e.g., by NP-HPLC) is followed by mass spectroscopy analysis. In some embodiments, the eluent from NP-RP-HPLC is analyzed directly with ESI-oaTOF MS for on-line molecular weight determination as well as relative peak abundance in the sample. In other embodiments, the proteins are separated and detected by UV absorption. In yet other embodiments, the eluting proteins are collected and the fractions digested with trypsin so that the resulting tryptic peptides can be mapped with MALDI-TOF MS or ESI-QIT-reTOF MS. In still further embodiments, the protein fraction are also sized on MALDI-TOF MS for protein molecular weight.

The present invention is not limited by the nature of the mass spectrometry technique utilized for such analysis. For example, techniques that find use with the present invention include, but are not limited to, ion trap mass spectrometry, ion trap/time-of-flight mass spectrometry, quadrupole and triple quadrupole mass spectrometry, Fourier Transform (ICR) mass spectrometry, and magnetic sector mass spectrometry. Those skilled in the art will appreciate the applicability of other mass spectroscopic techniques to such methods.

For example, in some embodiments, proteins are analyzed simultaneously to determine molecular weight and identity. A fraction of the effluent from the separation step is used to determine molecular weight by either MALDI-TOF-MS or ESI oa TOF (LCT, Micromass) (See e.g., U.S. Pat. No. 6,002,127; herein incorporated by reference in its entirety). The remainder of the eluent is used to determine the identity of the proteins via digestion of the proteins and analysis of the peptide mass map fingerprints by either MALDI-TOF-MS or ESI oa TOF. The molecular weight protein map is matched to the appropriate digest fingerprint by correlating the molecular weight total ion chromatograms (TIC's) with the UV-chromatograms and by calculation of the various delay times involved. The UV-chromatograms are automatically labeled with the digest fingerprint fraction number. The resulting molecular weight and digest mass fingerprint data can then be used to search for the protein identity via web-based programs like MSFit (UCSF).

In some embodiments, proteins are transferred to the mass spectroscopy step via an automated sample handling system. In some embodiments, data is automatically transferred to analysis software for the generation of protein profile maps.

C. Software and Data Presentation

The data generated by the above listed techniques may be presented as 1-D mass maps of intact proteins. In some embodiments, MaxEnt (version 1) software and Mass Lynx version 3.4 (Micromass) are used to analyzed mass spectroscopy data. The protein molecular weights are determined by MaxEnt deconvolution of multiply charged protein umbrella mass spectra that are obtained by combining anywhere from 10 to 60 seconds of data from the initial total ion chromatogram (TIC). All deconvoluted mass spectra from a given TIC are added together to produce one mass spectrum for each TIC.

In some embodiments, the data generated in the mass spectroscopy analysis (e.g., TIC's or integrated and deconvoluted mass spectra) are converted to ASCII format and then plotted vertically, using a 256 step gray scale, such that peaks are represented as darkened bands against a white background.

In other embodiments, a color coded 1-D protein profile mass map is generated from differential display of protein molecular weights. In some embodiments, the image is displayed by a computer system as a color-coded mass map, where the intensity of the protein bands corresponds to colors of the rainbow, increasing from blue to green to yellow to red. Thus, the image provides a protein expression pattern that can be used to locate proteins that are differentially displayed in different samples (e.g., cells representing different stages of a cancer). Naturally, the image can be adjusted to show a more detailed zoom of a particular region or the more abundant protein signals can be allowed to saturate thereby showing a clearer image of the less abundant proteins. As the image is automatically digitized it may be readily stored and used to analyze the protein profile of the cells in question. Protein bands on the image can be hyper-linked to other experimental results, obtained via analysis of that band, such as peptide mass fingerprints and MSFit search results. Thus all information obtained about a given 1-D image, including detailed mass spectra, data analyses, and complementary experiments (e.g., immunoaffinity and peptide sequencing) can be accessed from the original image.

The data generated by the above-listed techniques may also be presented as a simple read-out. For example, when two or more samples are compared (e.g., cancerous and non-cancerous cells), the data presented may detail the difference or similarities between the samples (e.g., listing only the proteins that differ in identity or abundance between the samples). In this regard, when the differences between samples (e.g., cancerous and non-cancerous cells) are indicative of a given condition (e.g., cancer cell), the read-out may simply indicate the presence or identity of the condition. In one embodiment, the read-out is a simple +/− indication of the presence of particular proteins or expression patterns associated with a specific condition that is to be analyzed.

A useful feature of the liquid phase method of the present invention is the capability of the high resolution mass spectrometry to quantitate which allows the observer to record relative levels of each form of a given protein. Consequently, it is contemplated that one can determine the relative abundances of the phosphorylated and non-phosphorylated forms of a given protein. In addition, post-translational modifications such as phosphorylation can be found by searching the data for intervals of some integer value times 80 Da.

With a mass resolution of 5000 Da, a 50000 Da protein can be resolved from a 50010 Da protein. Clearly, single phosphorylations on entire proteins can be observed with this level of resolution. Quantitative comparison between 1-D images can be achieved by spiking samples with known amounts of standard proteins and normalizing images through landmark proteins. Thus, the observer can detect significant abundance changes in the protein profiles of different samples.

D. Automation

In some embodiments of the present invention, one or more (e.g. all) of the above described steps are automated, for example, into one discrete instrument. In preferred embodiments, an automated on-line sample handling system fully integrates the separation and analysis steps of the methods of the present invention. The sample flows directly from the separation phase (e.g., NP-RP HPLC) to the mass spectrometer. The automation of protein separation increases efficiency and speed as well as decreases sample loss or potential contamination that may occur through handling.

In some embodiments of the present invention, sample analysis is automated and integrated with the centralized control network. For example, mass spectroscopy data is transferred to an integrated computer system containing software for the generation of 1-D protein maps. The integrated computer system is also capable of searching databases and generating a report. The report is provided to the operator in a format that is customized to the particular application. For example, the report may identify specific proteins that are present in one sample (e.g., a cancer cell line) and absent in another (e.g., a control non-cancerous cell line) or are present at different abundances between the two samples.

E. Presentation of Results

In some preferred embodiments of the present invention, the information generated by the protein profile display is distributed in an coordinated and automated fashion. In some embodiments of the present invention, the data is generated, processed, and/or managed using electronic communications systems (e.g., Internet-based methods).

In some embodiments, a computer-based analysis program is used to translate the raw data generated by the protein profile map (e.g., identity and abundance of proteins in a sample) into data of predictive value for the clinician (e.g., the existence of a malignancy, the probability of pre-cancerous cells becoming malignant, or the type of malignancy). The clinician (e.g., family practitioner or oncologist) can access the predictive data using any suitable means. Thus, in some preferred embodiments, the present invention provides the further benefit that the clinician, who is not likely to be trained in molecular biology or biochemistry, need not understand the raw data of the protein profile map. The data is presented directly to the clinician in its most useful form. The clinician is then able to immediately utilize the information in order to optimize the care of the subject.

The present invention contemplates any method capable of receiving, processing, and transmitting the information to and from medical personal and subject. For example, in some embodiments of the present invention, a sample (e.g., a biopsy) is obtained from a subject and submitted to a protein profiling service (e.g., clinical lab at a medical facility, protein profiling business, etc.) to generate raw data. Once received by the protein profiling service, the sample is processed and a protein profile is produced (i.e., protein expression data), specific for the condition being assayed (e.g., presence of specific cancerous or pre-cancerous cells).

The protein profile data is then prepared in a format suitable for interpretation by a treating clinician. For example, rather than providing raw protein profile data, the prepared format may represent a risk assessment or probability of developing a malignancy that the clinician may use or as recommendations for particular treatment options (e.g., surgery, chemotherapy, or observation). The data may be displayed to the clinician by any suitable method. For example, in some embodiments, the protein profiling service generates a report that can be printed for the clinician (e.g., at the point of care) or displayed to the clinician on a computer monitor.

In some embodiments, the protein profile information (e.g., protein profile map) is first analyzed at a point of care or at a regional facility. The raw data is then sent to a central processing facility for further analysis into clinician. The central processing facility provides the advantage of privacy (all data is stored in a central facility with uniform security protocols), speed, and uniformity of data analysis. For example, using an electronic communication system, the central facility can provide data to the clinician, the subject, or researchers. The use of an electronic communications system allows protein profile data to be viewed by clinicians at any location. For example, protein profile data could be accessed by a specialist in the type of disease (e.g., cancer) that the subject is affected with. This allows even remotely located subjects to have their protein profiles analyzed by the leading experts in a particular field. The present invention thus provides a coordinated, timely, and cost effective system for obtaining, analyzing, and distributing life-saving information.

II. Differential Protein Expression in Human Breast Cancer Cell Lines

In some embodiments, the present invention provides methods of utilizing the methods of the present invention to rapidly separate proteins from whole cell lysates of human breast cancer cells and detect the protein molecular weights on-line (e.g., using an ESI-oaTOF MS). In some embodiments, the present invention provides methods of detecting proteins that are more highly expressed in certain malignant and pre-malignant cancers. In some embodiments, the molecular weight profiles are displayed as a mass map analogous to a virtual "1-D gel" and differentially expressed proteins are compared by image analysis. In other embodiments, the separated proteins are detected by UV absorption and differentially expressed proteins are quantitated. In yet other embodiments, the eluting proteins are collected in the liquid phase, and the molecular weight and peptide maps determined by MALDI-TOF identification.

Figure 2:
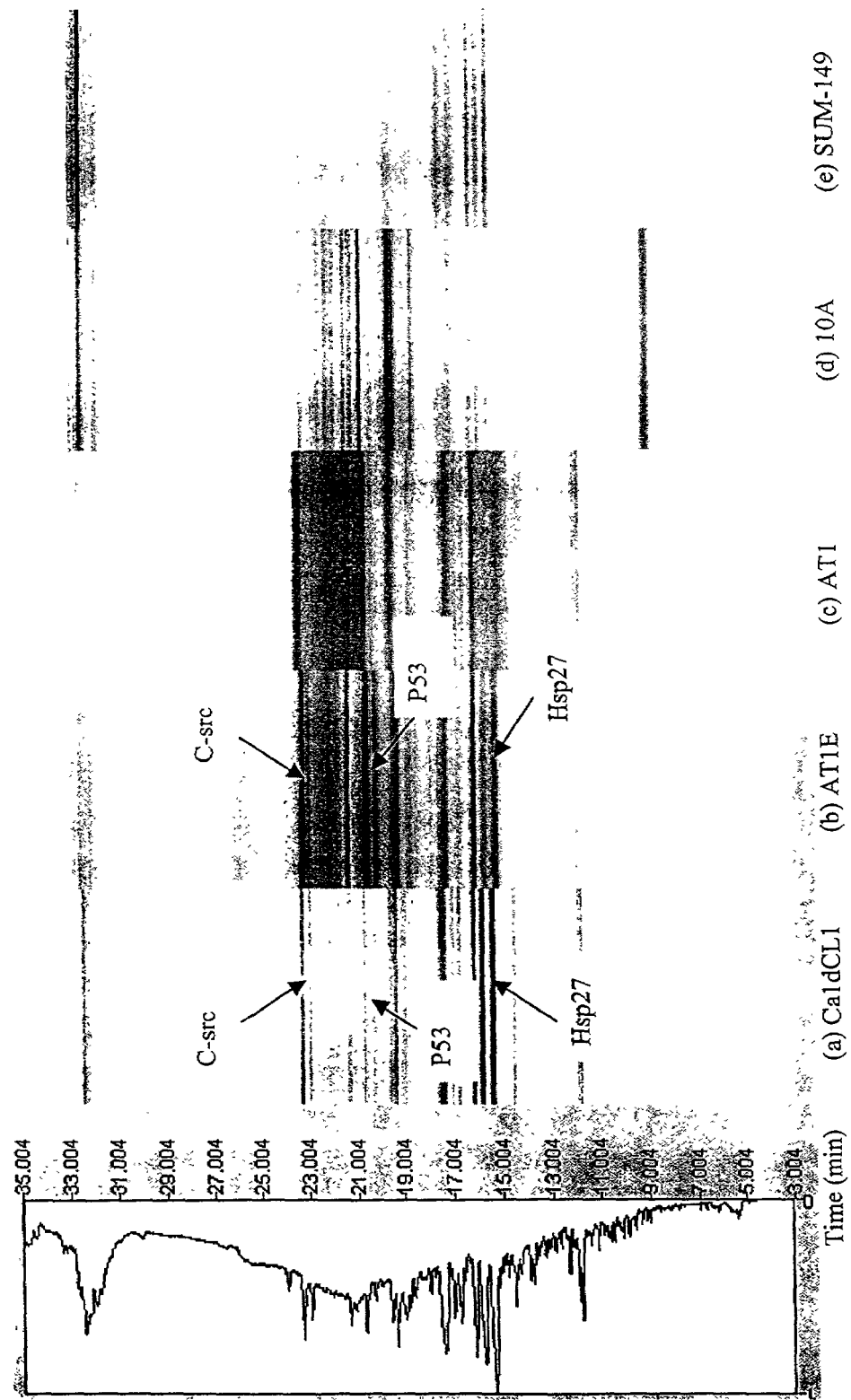
FIG. 2 shows a 2-D image of NP-RP-HPLC-ESI-oaTOF total ion chromatogram profiles of (a) CaldCL1, (b) AT1E, (c) AT1, (d) 10A, and (e) SUM-149 human breast whole cell lysates. Peak intensity is depicted in different shades of gray. The inset shows the chromatogram for (a) CaldCL1.

Illustrative Example 3 demonstrates the use of the methods of the present invention to identify proteins differentially expressed in human breast cancer cell lines. Example 3A describes separation of proteins from various cancerous and pre-cancerous human breast cancer cell lines by HPLC and on-line detection by ESI-oa-TOF MS. FIG. 2 shows a 1-D image of the nonporous separation of five different whole cell lysates of human breast cancer cell lines. The intensity of the protein peaks is shown in different shades of gray so that the images provide a differential display of key oncoproteins according to their relative abundance.

Figure 3:
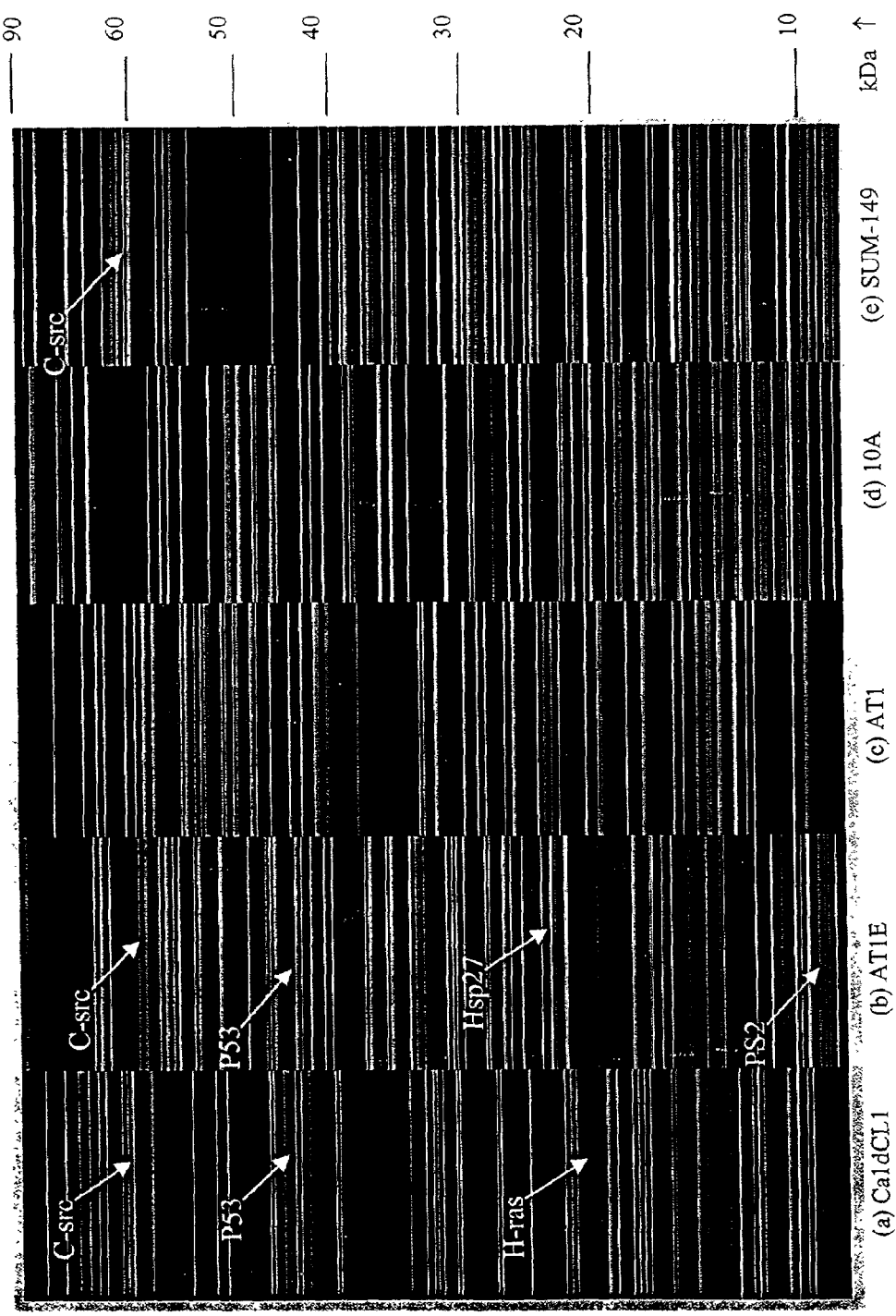
FIG. 3 shows a 1-D image of protein molecular weight for (a) CaldCL1, (b) AT1E, (c) AT1, (d) 10A, and (e) SUM-149 human breast whole cell lysates. The right bar shows the molecular weight scale (kDa) and the peak intensity is depicted in a color-coded mass map, where the intensity increases from shades of violet to indigo, then from shades of blue to green.

In FIG. 3 is shown a 1-D image of the proteins from the various breast cancer cells lines displayed by molecular weight as determined by the LCT. This figure is very much an analogue to a 1-D gel, but provides very accurate molecular weight information with much improved resolution compared to a gel. The image is displayed by the computer as a color-coded mass map, where the intensity increases from shades of violet to indigo, then from shades of blue to green. The image provides a means of directly comparing protein expression in different cell lines with respect to quantitative expression and changes in protein structure through changes in molecular weight. The 1-D column separation methods of the present invention thus provide a means of rapidly monitoring changes in proteins that are highly expressed in cancerous cell lines.

Illustrative Example 3B provides methods for determining the identify of differentially expressed proteins by using UV detection. The point in the gradient at which each peak is detected is highly reproducible. The molecular weights determined were correlated with the gradient of the separation, and the proteins were collected in the liquid phase at the corresponding point in the gradient. The proteins were then digested via trypsin or CNBR and analyzed by MALDI-MS. In Table 1 are listed a selection of the key proteins and their molecular weight as determined by MALDI-MS.

The present invention also provides methods of assaying the effects of various compounds (e.g., hormones or environmental toxins) on the protein expression patterns of cancer cell lines. Previous studies have shown that estrogens stimulate the proliferation of many breast tumors and cell lines derived from them (Maggiolini et al., Cancer Research 59:4864 [1999]). Estrogens also stimulate growth of normal and malignant breast cells in tissue culture (Thomas et al., J. Nat Cancer Inst., 69:1017 [1982]). Further studies have also shown that estrogen is associated with a significant increase in breast cancer risk. These data taken together with other epidemiological data and laboratory evidence suggest that estrogen is a promoter of mammary tumors (Mils et al., Cancer 64:591 [1989]). In addition, estradiol-induced inactivation of p53 may be involved in the tumorigenesis of estrogen-dependent neoplasm (Molinari et al., Cancer Research 60:2594 [2000]).

Illustrative Example 3C describes the effects of estradiol exposure on AT1 cells. Proteins from cells exposed to estradiol and control cells not exposed were separated analyzed for molecular weight by MALDI-MS. In addition, part of the fraction was digested by trypsin or CNBR for identification by MALDI-MS and database searching. The protein profiles observed in FIG. 4 are clearly different between the AT1 and AT1E samples. A list of some of the more abundant proteins that have been identified by peptide mapping and MALDI-MS are listed in Table 2. There are several proteins for which expression is induced by estradiol, including PS2 estrogen inducible protein, estradiol 17 β-dehydrogenase 7 and ERR1 estrogen receptor-like 1. Other proteins such as HSP 27 become much more highly expressed in response to estradiol.

Recent studies (Tesarik et al., Steroids, 64:22 [1999]) have shown that estrogen/estradiol stimulates cell proliferation in breast tumors and cell lines derived from them, thus accelerating these cells towards malignancy. Indeed, in this example, the expression of key oncoproteins in AT1E starts to resemble those of the highly malignant cell line CaldCLI. This change in expression is evident in the online ESI-TOF-MS protein profile of FIG. 3 and also in the UV chromatogram protein profile. As expected the malignant and premalignant protein profiles vary markedly from the normal (immortalized) cell line MCF10A. The present invention thus provides methods of monitoring pre-cancerous cells for their level of malignancy in response to certain external stimulants such as estrogen. For example, the protein expression pattern of pre-cancerous cells identified in a patient could be monitored more closely if they were taking a compound known to effect cell proliferation.

The over-expression of the c-src oncogene has been observed in several types of cancers including breast and colon cancer (Rosen et al., J. Biol. Chem., 261:13754 [1986]; Ottenhoff-Klaff et al., Cancer Res. 52:4773 [1992]; Brown et al., M. T.; Cooper, J. A., Biochimica et Biophysica acta 1287:121 [1996]; Mao et al., Oncogene 15:3083 [1997]; and Egan et al., Oncogene 18:1227 [1999]). Elevated levels of c-src kinase activity have been attributed to changes in phosphorylation patterns at Tyr 530 (Brown et al., Biochimica et Biophysica Acta, 1287:121[1996]; Egan et al., Oncogene 18:1227 [1999]). C-src kinase activity has been implicated in tumorigenesis and metastasis in these cancers (Mao et al, Oncogene 15:3083 [1997]). It is also suspected that c-src is responsible for phosphorylating other proteins, thus changing their functions in cell cycle regulation (Brown et al., Biochimica et Biophysica Acta, 1287:121[1996]).

Figure 5:
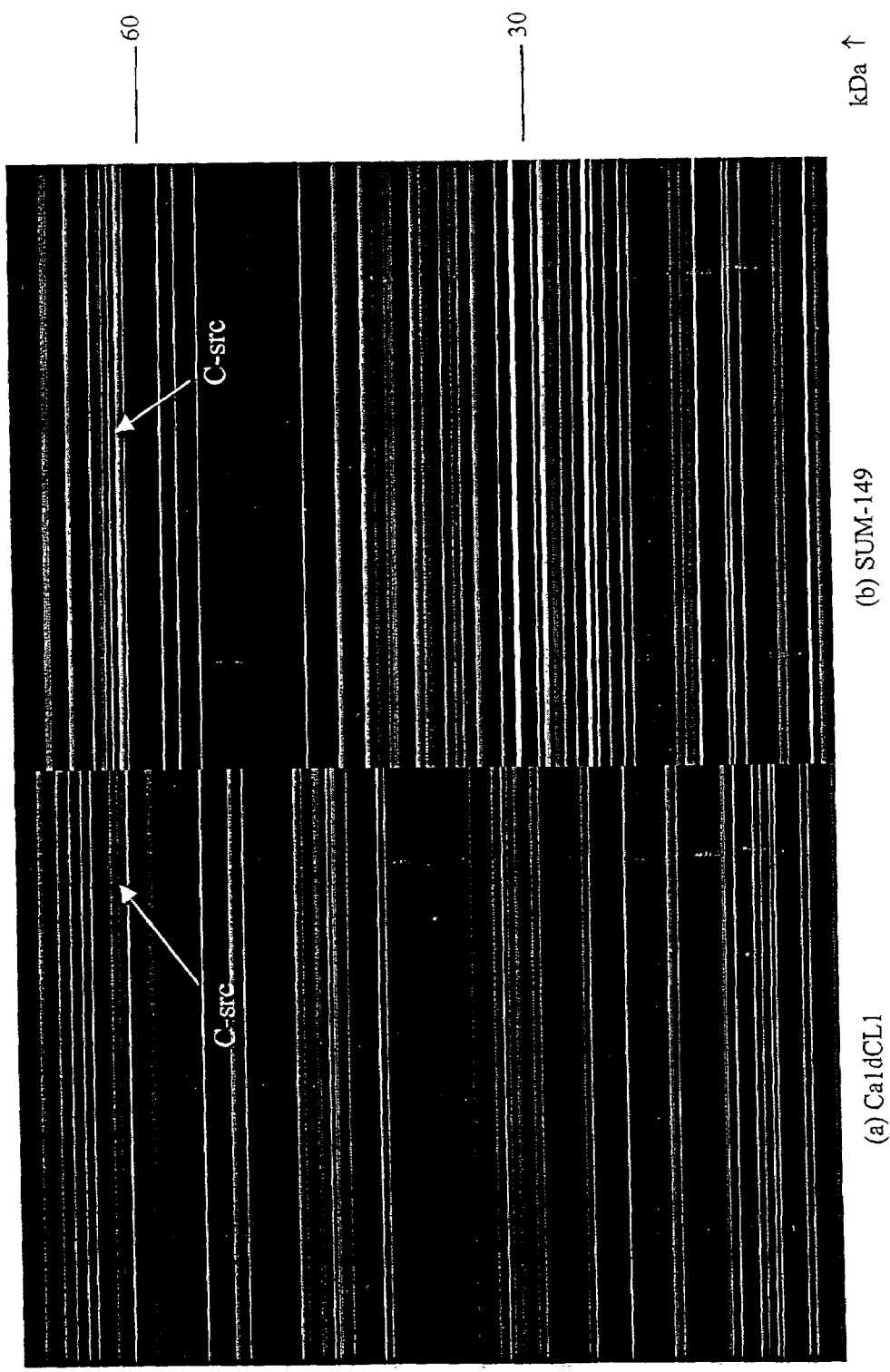
FIG. 5 shows a zoom-in 1-D image of protein molecular weight for (a) CaldCL1 and (b) SUM-149 malignant human breast whole cell lysates. The right bar shows molecular weight scale (kDa) while the peak intensity is depicted in a color-coded mass map.

Illustrative Example 3C (FIG. 3) demonstrates that the molecular weight of c-src in AT1E is 60,540 Da while that in CaldCL1 is 62,780 Da. The database value is 59,835 Da. The two malignant cell lines, CaldCL1 and SUM-149, also show distinct differences in protein expression as seen in FIGS. 2 and 3. FIG. 5 shows a zoom-in 1-D image (from FIG. 3) comparing CaldCLI and SLTM-149. The molecular weight of c-src in SUM-149 is 61,860 Da.

Illustrative Example 3C further describes the study of differences between c-src in the AT1 and AT1E cell lines. More than 45 peptides from c-src were detected and analyzed and as expected most of them are the same between AT1 and AT1E cell lines. Several peptides were identified that are modified differently between AT1 and AT1E. It appears that there are differences in the phosphorylation patterns of the peptides detected. It is contemplated that the shift in molecular weight and the change in phosphorylation pattern as a function of cancer progression may be related to changes in protein structure and function that affect protein cascades leading to tumorigenesis and metastasis (Brown et al., Biochimica et Biophysica Acta, 1287:121[1996]; Egan et al, Oncogene 18:1227 [1999]). The present invention thus provides methods of identifying modifications (e.g. phosphorylation) present or absent only in pre-cancerous or cancerous cells.

It should be noted that other important proteins also show changes in molecular weight as a function of cancer progression. In particular, p-53 is a tumor suppressor protein that is involved in controlling the cell cycle. Wild-type p-53 is involved in maintaining genomic integrity and stability, where the p-53 searches for mutations in the DNA sequence (Gottleib and Oren, Biochimica et Biophysica Acta 1287:77 [1996]; "Tumor Suppressor Genes" in Cancer Biology, 3rd Ed., by Raymond W. Ruddon, Oxford University Press, N.Y. 1995, pgs.318–340). If such mutations are found a series of events either leads to DNA repair or if repair is not effected then to cell death (Gottleib and Oren, Biochimica et Biophysica Acta 1287:77 [1996]; "Tumor Suppressor Genes" in Cancer Biology, 3rd Ed., by Raymond W. Ruddon, Oxford University Press, N.Y. 1995, pgs.318–340). This mechanism prevents the build-up of mutations in normal cells. However, if the p-53 is phosphorylated in critical sites then it does not function as a tumor suppressor and the cell divides without control or becomes immortalized ("Tumor Suppressor Genes" in Cancer Biology, 3rd Ed., Raymond W. Ruddon, Oxford University Press, N.Y. 1995, Ch. 8 pp. 318–340). The measured molecular weight of p-53 in FIG. 3 as a function of progression indicates changes in structure that may affect its function.

Another protein associated with various types of cancer is Hsp 27 (Tetu et al., Breast Cancer Research & Treatment 36:93 [1995]). Studies have shown that Hsp 27 can be induced or activated by excess estrogen/estradiol (Porter et al, Molecular Endocrinology 10:1371 [19961]). In FIG. 2 there are both changes in expression and molecular weight observed in HSP 27 as a function of progression.

The 1-D images generated by the methods of the present invention provide a direct method of comparing the more highly expressed proteins in different cell lines at different stages of neoplastic progression.

It is demonstrated by illustrative Example 3 that the expressed protein profiles change during neoplastic progression and that many oncoproteins are readily detected. It is also shown that the response of premalignant cancer cells to estradiol can be rapidly screened by this method demonstrating significant changes in response to an external agent. Ultimately, the proteins can be studied by peptide mapping to search for post-translational modifications of the oncoproteins accompanying progression. The present invention thus provides improved methods for the study the response of cells in terms of protein expression to such external stimulants. In addition, the present invention provides methods of identifying pre-cancerous cells based on protein expression patterns, thus providing for intervention before malignancies have developed. Early detection allows for increased treatment options, decreased morbidity, and decreased mortality.

The present invention also provides the ability to monitor changes in protein expression in cancer cells in response to pharmacological, environmental or chemotherapeutic agents. The use of the 1-D liquid separation can provide identification of the major changes in protein expression due to such external agents.

III. Drug Screening

In some embodiments, the systems and methods of the present invention find use in drug screening applications. For example, in some embodiments, the effect of one or more test compounds (e.g., pharmacological agents or environmental toxins) on the level of expression of one or more specific protein species is investigated. In some embodiments, the phosphorylation state of one or more proteins in the presence or absence of the test compound is investigated. In some embodiments, a protein profile map that highlights only the specific protein(s) of interest is generated.

In other embodiments, the effect of one or more compounds on the global expression pattern of one or more samples (e.g., cell types) is investigated. Protein profile maps can be compared to maps generated from known cell types (e.g., differentiated or non-differentiated cell types or cancerous or non-cancerous cell types) in order to determine the state of the samples following exposure to the research compound.

The drug screening methods of the present invention are amenable to high-throughput screening analysis. The computer generated protein profile maps of the present invention allow for the efficient analysis and comparison of large numbers of samples.

Experimental

The following examples serve to illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); °C. (degrees Centigrade); PBS (phosphate buffered saline); and Geno Technology (Geno Technology Inc., St. Louis, Mo.).

EXAMPLE 1

MCF10 Cell Line

This example describes the properties, growth procedures, and lysis procedures of cell lines used in the following experiments. The MCF10 cell lines that were used in these experiments were obtained from spontaneously immortalized breast epithelial cells from a patient with fibrocystic disease (Soule et al., Cancer Research 50:6075 [1990]). The MCF10AT1 cell line produces xenograft lesions in immune deficient mice that resemble high risk proliferative breast disease in women. These lesions spontaneously progress to invasive carcinoma at about 25% incidence during the life of the host mouse (Miller et al., J. NatL Cancer Inst., 85:1725 [1993]; Dawson et al, Am. Journal of Pathology 1996, 148, 313–319.). Progression of the MCF10AT1 lesions in mice is accelerated by estradiol (Shekhar et al., Int. J Oncology 13:907 [1998]). Because exposure to estrogen is a generally accepted risk factor for breast cancer development, MCF10AT1 serves as an important model to test the effect of estrogen on the development of human breast cancer.

A. Cell Growth

MCF10AT1 cells are grown in monolayer on plastic in DMEM/F12 medium (1:1 mixture of Dulbecco's modified Eagle's medium and Ham's F-12 medium) supplemented with 5% hourse serum, 10 μg/ml insulin, 20 ng/ml epidermal growth factor, and 0.5 μg/ml hydrocortisone. Approximately 50% confluent cell monolayers were treated with $10^{-9}$ estradiol for 24 hours, collected by scraping, washed two times by centrifugation in phosphate buffered saline, and stored at −70° C. Estradiol was dissolved in absolute ethanol and controls were treated with the same volume of ethanol so that the final concentration of ethanol during treatment was 1%. A fully malignant metastatic variant, MCF10CaldCL1, was derived from premalignant MCF10AT xenografts (Santner et al., Proc. Am. Assoc. Cancer Res. 39:202 [1998]). Cells were maintained in a humidified $CO_2$ incubator at 37° C., and adherant cells harvested in log phase (75–80% confluence). In order to harvest the cells, the growth media was aspirated and the cells gently washed with PBS, prior to scraping with a rubber policeman. The cells were immediately frozen (−70° C.) upon removal from the tissue culture dishes.

Protein profiles were also examined for SUM-149, which is a recently developed cell line form a primary infiltrating ductal carcinoma of the breast from a patient with locally advanced disease. The culture medium for SUM-149 consisted of Ham's F-12 with 5% fetal bovine serum, insulin, and hydrocortisone.

B. Cell lysis

Proteins were extracted from cells using a chemical lysis procedure. The lysis buffer contained 6M guanidine-HCL, 20 mM n-octyl β-D-glucopyransoside and 50 mM Tris. The cells were vortexed vigorously and stored overnight at −20° C. The cells were then centrifuged at 17,000 rpm for 20 minutes. The supernatant was removed from the cellular material and re-centrifuged at high speed to remove any particulate. Lysate was preferably used within 48 hours. Protein concentration was assayed using the protein dot metric kit (Geno Technology).

EXAMPLE 2

Methods

This example illustrates some of the experimental methods utilized in the development of certain embodiments of the present invention.

A. Chemicals

The chemicals used in the following examples were used without prior purification. Acetone (HPLC grade) was obtained from Fisher (Fair Lawn, N.J.). Acetonitrile, guanidine hydrochloride (gu-HCl), α-cyano-4hydroxycinnamic acid (α-CHCA) trifluoroacetic acid (TFA), formic acid (FA), and octyl glucopyranoside (OCG) were from Aldrich (Milwaukee, Wis.). Trypsin was acquired from Promega (Madison, Wis.). Distilled and deionized water was obtained from Milli-Q reagent grade purification system from Millipore (Bedford, Mass.). The nitrocellulose (NC) used, Immobilin-NC pure was from Millipore.

B. HPLC

A Beckman (Fullerton, Calif.) System Gold HPLC was utilized. The pump (model 128) has a gradient solvent delivery module with built-in system controller. The detector was a programmable detector module (Model 166) with an analytical flow cell. The deuterium lamp provided a wide rage of detection from 190 to 700 nm. All separations in this work were monitored at 214 nm.

ODSIIIE and ODSI NP RP HPLC columns (Eichrom Technologies, Darien, Ill.) contained 1.5 μm C18 (ODSI) non-porous silica beads. Column dimensions were 4.6*33 mm (ODSIIIE) and 4.6*14 mm (ODSI). The RP-HPLC separations of proteins in the tumor cell lysate was performed via gradient elution of two solvents (Solvent A: Milli-Q water with 0.1% TFA; Solvent B:ACN with 0.1% TFA) with a flow rate of 1.0 mL/minute. The column was placed in a Timberline column heater and maintained at 60° C. The gradient profile used was as follows: 1) 0% for 1.5 min; 2) 0 to 10% acetonitrile (solvent B) in 2 minutes; 3) 10 to 60% B in 25 minutes; 4) 60 to 80% B in 5 minutes; 5) 80 to 100% B in 1 minute; 6) 100% B for 2 minutes; 7) 100 to 0% B in 1 minute. In order to obtain a reproducible separation profile, the sample was "conditioned" to the column environment by mixing the sample with an equivalent amount of water (0.1% TFA) in a 1:1 ratio. This acidifying step was performed prior to sample injection. Each injection contained an average of 20–30 μg of protein. The fractions collected were subsequently subjected to MALDI analysis to size the protein masses. Each of the peaks contained an average of 0.5–2.5 μg available for analysis after collection. The fractions were then digested by trypsin before undergoing pulse-delayed extraction (PDE) MALDI-TOF analysis to obtain their peptide maps.

C. MALDI-TOF MS

The TOF mass spectrometer employed in these studies was a modified Wiley-McLaren design with a four-plate acceleration stage (Whittal and Li, Anal Chem. 67: 1950 [1995]). It was capable of high voltage acceleration up to ±20 kV (R. M. Jordan Co., Grass Valley, Calif.). The laser source used to produce MALDI was a MINILITE 10 Hz Nd:YAG laser system (Continuum, Santa Clara, Calif.). All mass spectra were obtained using 355 nm radiation. The laser power density was estimated at $5 \times 10^6$ to $1 \times 10^7$ W/cm$^2$. The detector was a triple microchannel plate (MCP) detector (R. M. Jordon) which adapted a CuBe conversion dynode with post-acceleration (PA) capability up to ±12 kV in front of the MCP. The total ion acceleration across the TOF device may thus be >30 kV. The PA stage enhances the detection of heavy species, but at the expense of resolution. In addition, pulsed delayed extraction (PDE) was used to enhance the resolution for the analysis of the tryptic digests. The 1-m long flight tube was pumped to a base pressure of $8 \times 10^{-7}$ to $1 \times 10^6$ Torr by a diffusion pump (Varian Inc, Lexington, Mass.). Data was recorded using a LeCroy 9310AM (400 MHz) digital oscilloscope (LeCroy Corp., Chesnut Ridge, N.Y.) and was processed on a Gateway 586 computer.

D. ESI-oaTOF MS Analysis

An LCT (Micromass, Ltd., Manchester, UK) was used for online NP-RP-HPLC-ESI-oaTOF MS analysis. The MS parameters were set as follows: Source–Capillary=3000 V; Sample Cone 45 V, RF lens=800 V; Extraction Cone=2 V; Desolvation Temperature=300° C., and Source Temperature=120–150° C. The Beckman HPLC system (as described above) was interfaced with the LCT using the NP column separations. The solvents for the mobile phase were (solvent A) Milli-Q water with 0.1% TFA+0.2 to 0.3% FA and (solvent B) acetonitrile with 0.1% TFA+0.2 to 0.3% FA with a flow rate of 0.5 mL/min where the temperature of the NP column was maintained at 65° C. in a Timberline column heater. The gradient profile used for solvent B was generally as follows: 5% for 1.5 min; 5 to 20% in 2 min; 201 to 30% in 4 min; 30 to 45% in 10 min; 45 to 60% in 7.5 min; 60 to 70% for 4 min; 70 to 100% in 1 min, 100% for 2 min, 100 to 5% in 1 min, 5% for 2 min. The 0.5 mL/min was split to a 1:1 ratio before entering the electrospray source. The chromatograms generated were deconvoluted using MaxEnt software (Micromass).

E. ESI-QIT-reTOF MS Analysis

The experimental setup consists of an HPLC separation system (Star 9012, Varian Associates, Inc., Walnut Creek, Calif.) interfaced to an electrospray ionization source with detection using a quadrupole ion trap reflectron time-of-flight mass spectrometer (Model C-1251, R. M. Jordan Co., Grass Valley, Calif.). This hybrid mass spectrometer has been described in detail in previous work (Michael et al., Anal Chem., 65:2614 [1994]). Mass spectra were acquired using a DOS-based Borland Pascal software program written in-house (Li et al., J. Am. Soc. Mass Spec., 9:701 [1998]), and digitization of the mass spectrum was performed by an 8-bit 250 MHz analog bandwidth transient recorder (Model 9846, Precision Instruments, Knoxville, Tenn.). Ions were accumulated for 333 ms and subsequently ejected by applying a +2000V dc pulse to the entrance endcap (DEI GRX-3.0K-H, Directed Energy, Fort Collins, Colo.).

The liquid chromatography system was operated at 200 μL/min with a prime/purge valve located immediately before the injection valve to split the mobile phase in a 3:1 ratio. The 10 cm×250 μm i.d. column was packed with porous 5 μm C18 particles (Vydac, Hesperia, Calif.) in-house using the slurry packing method (Qian et al., Anal Chem., 67:2870 [1995]). Mobile phase A consisted of Milli-Q $H_2O$ with 0.1% formic acid and mobile phase B of acetonitrile with 0.1% formic acid. The separation gradient for mobile phase B was as follows: 5% for 5 min, 5% to 20% in 5 min, 20% to 60% in 25 min, 60% to 100% in 15 min, 100% for 5 min, 100% to 5% in 5 min, and 5% for 15 minutes.

F. Database Searching Procedure for Protein Identification

The MS-Fit sequence database located in the Protein Prospector program was used for protein identification by entering the peptide masses generated by tryptic digestion. The program is available on the Internet at the Internet World Wide Web site of the Protein Prospector at the University of California-San Francisco. Subsequently, other relevant parameters such as protein species, molecular weight and pI range are also entered in order to narrow down the search. In the illustrative examples of the present invention, Homo sapiens was chosen as the species. Since these proteins were obtained from HPLC, no isoelectric point (pI) information was available. Thus, the pI range was set between 3 and 10. The range of molecular weight values for each search was determined by MALDI-TOF or ESI-TOF analysis. The tolerance for the search of peptides against the database was set at 2 Da for MALDI-MS spectra and 0.5 Da for QIT-reTOF-MS spectra.

EXAMPLE 3

Mass Mapping of Proteins from Premalignant and Malignant Cell Lines

This Example describes multidimensional NP-RP-HPLC-MS analysis of human breast cell lines representing different stages of neoplastic progression. An overview of the methodology is shown in FIG. 1. The cell lines utilized included MCF10A, which is a "normal," but immortalized, cell line where the cell line keeps dividing but the phenotype is non-tumorigenic. The AT1 sample is considered a "premalignant" stage in progression. The AT1E lysate is the AT1 cell line that has been exposed to estradiol. The CaldCL1 is a highly malignant, tumorigenic cell line. These four cell lines have developed from a common precursor with essentially the same genetic background. The SUM-149 sample is a highly malignant cell line that has been developed from breast cancer tissue from a different patient and is included for comparison.

A. NP-HPLC and ESI-oa-TOF MS Analysis

An ODS2 nonporous column was used to separate the protein content of the cell with on-line detection by ESI-oa-TOF MS using the Micromass LCT. The total ion chromatogram (TIC) mode of operation was used to collect the data. FIG. 2 shows a 1-D image of the nonporous separation of five different whole cell lysates of human breast cell lines. A typical TIC of the nonporous separation of the CaldCLI cell line is shown in the inset of FIG. 2. The y-axis in the 1-D image of FIG. 2 represents the elution time of each peak in the chromatogram. Each of the bands in the 1-D image corresponds to an eluting protein peak. The intensity of the protein peaks is shown in different shades of gray so that the images provide a differential display of key oncoproteins-according to their relative abundance.

In FIG. 3 is shown a 1-D image of the proteins displayed by molecular weight as determined by the LCT. In FIG. 2, the bands represent the TIC, where the corresponding ESI mass spectra are ladders of multiply charged peaks generated in the electrospray process. These ladders are processed by the MaxEnt program to provide the molecular weights, which correspond to the protein bands of FIG. 3. The intensity of the protein peaks has been normalized relative to common peaks in each sample. The image is displayed by the computer as a color-coded mass map, where the intensity increases from shades of violet to indigo, then from shades of blue to green. The image provides a means of directly comparing protein expression in different cell lines with respect to quantitative expression and changes in protein structure through changes in molecular weight. This is shown in FIG. 3 in comparison of the bands for c-src and p53 where large changes in expression are observed and where shifts in molecular weight were also detected.

In the images of FIGS. 2 and 3, approximately 75–80 unique protein masses over a mass range of 5 to 90 kDa were determined using the MaxEnt software for each cell line. Due to the dynamic range of the 1-D image in FIG. 3, only the more highly expressed proteins appear in bands whereas the dark areas represent protein bands in extremely low intensity. It should also be noted in the TIC of FIG. 2 that the baseline of the separation never returns to zero. The mass spectrum shows that there are protein peaks everywhere (i.e., in both the peaks and the valleys). This is to be expected since there are thousands of proteins expressed in these cells. The limited number of peaks observed is either due to the fact that many of the lower level proteins are lost during the MaxEnt process or that many of the peaks in the baseline have not been analyzed. The results of this experiment (FIG. 2) show that a variety of proteins are expressed very differently in the progression of cancer.

B. NP-HPLC with UV Detection and MALDI-MS Analysis

The data in FIGS. 2 and 3 provide maps from which protein expression can be compared, but they do not in themselves provide protein identification. In order to obtain such identification, the nonporous separation was performed using UV detection. The point in the gradient at which each peak is detected is highly reproducible. The molecular weight of the proteins detected by the LCT during the on-line separation is not known since only multiply charged envelopes are obtained, and is determined later using MaxEnt. The molecular weights determined were correlated with the gradient of the separation, and the proteins were collected in the liquid phase at the corresponding point in the gradient. The proteins were then digested via trypsin or CNBR and analyzed by MALDI-MS. In Table 1 are listed a selection of the key proteins and their molecular weight as determined by MALDI-MS. It should be noted that MALDI and ESI methods are complementary for determination of molecular weight in these samples. Some proteins are detected by both methods; however, some proteins are detected only by off-line liquid collection and MALDI-MS, and others are detected by on-line ESI-MS. The results of this experiment indicate that it is possible to determine the identity of proteins detected by on-line ESI-MS.

TABLE 1

Proteins identified in AT1E that are differentially expressed compared to AT1:

| Protein Name | Molecular Weight (Da): SwissProtein Database | AT1E | Detected AT1 | CaldCL1 |
|---|---|---|---|---|
| H-ras Transforming protein P21 | 21298 | 21700 | not detected | 21695 |
| PS2 Estrogen-inducible protein | 9149 (unprocessed precursor) | 8960 | not detected | not detected |
| HS27 Heat shock protein | 22327 | 22620 | 22560 | not detected |
| Estradiol 17 β-dehydrogenase 7 | 38206 | 38220 | not detected | 38440 |
| β-Actin or γ-Actin | 41737,41793 | 42010 | 41710 | 42100 |
| P53 Cellular tumor antigen | 43653 | 44380 | not detected | 44880 |
| ERR1 Estrogen receptor-like1 | 55439 | 55960 | 55770 | 55640 |
| C-src Tyrosine-protein kinase | 59703 | 60540 | 60060 | 61860 |
| Triosephosphate isomerase TIM | 26670 | 26940 | not detected | 26850 |

C. The Effect of Estrogen on Protein Expression

Figure 4A:
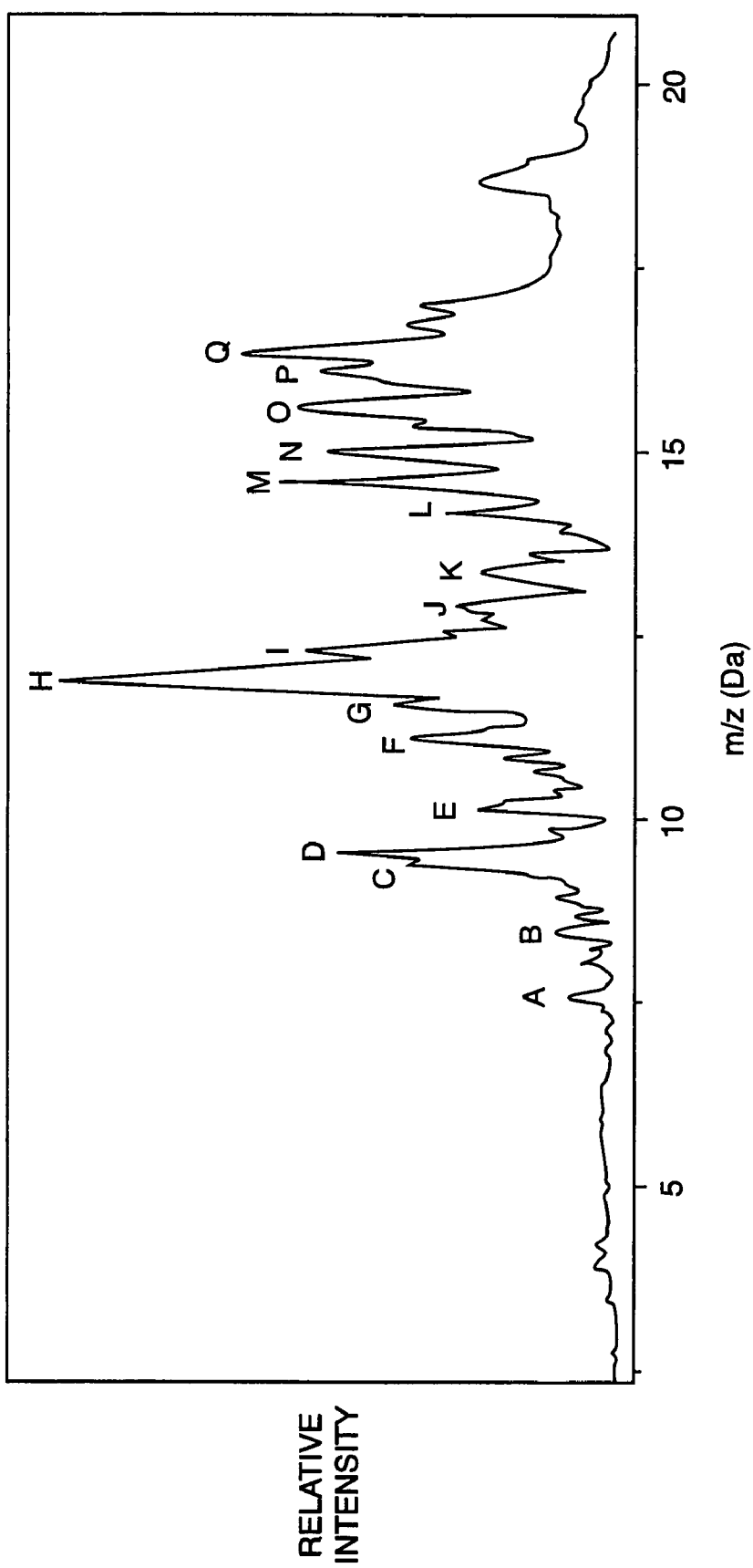
FIG. 4 shows 2-Column NP-RP-HPLC protein profiles of (a) AT1E and (b) AT1 whole cell lysates.
Figure 4B:
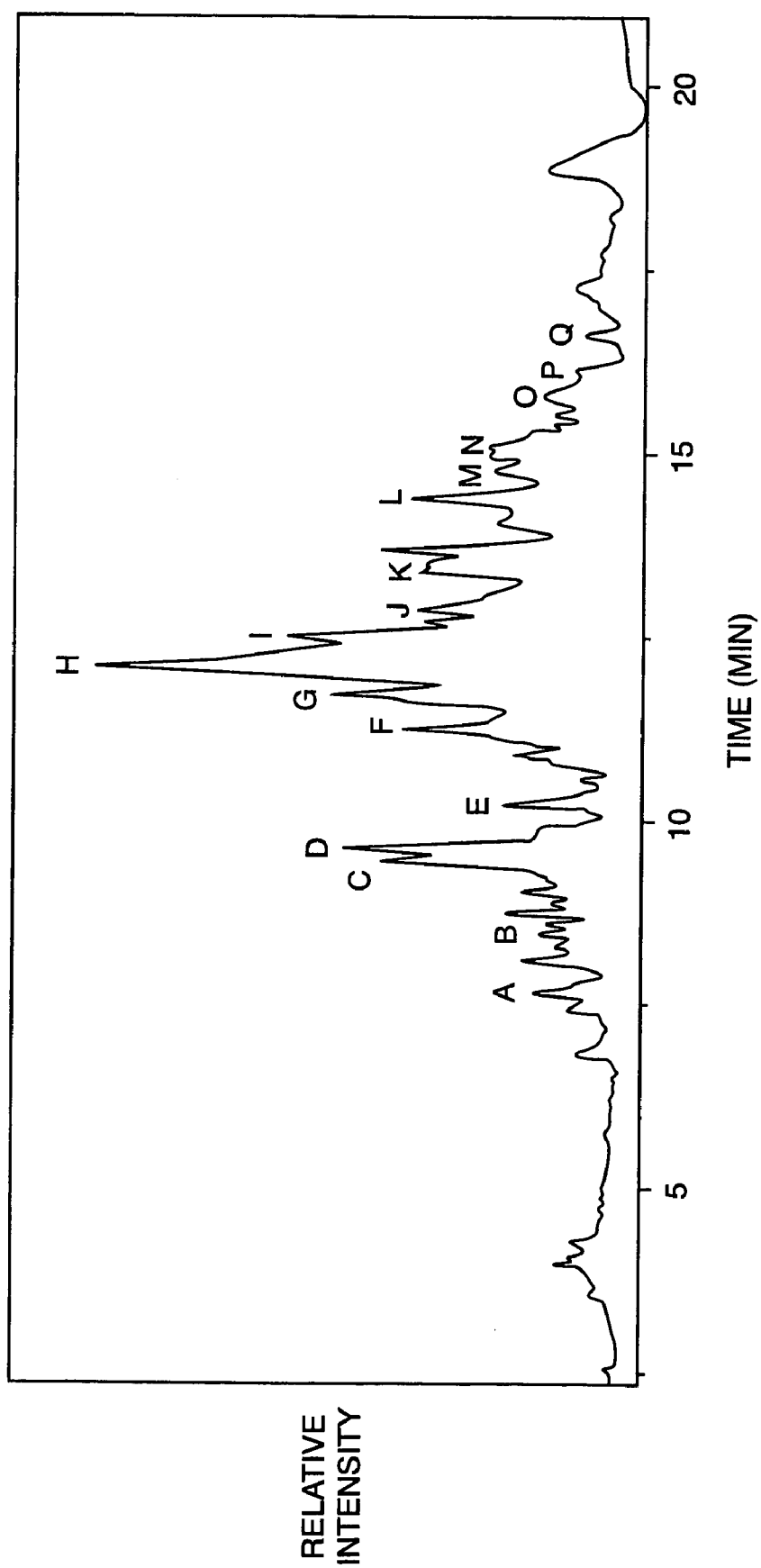

This example describes the effects of estradiol exposure on protein expression in AT1 cells. FIGS. 4A and 4B show the chromatograms obtained by nonporous separation of whole cell lysates of AT1 and AT1E with UV detection at 214 mn. These separations were performed with a 2-column tandem system: an ODSIIIE column followed by an ODSI column. This method is used in order to optimize the loadability and the amount of sample collected for detailed sequencing experiments. The 2-column separation was performed at the expense of resolution in the separations.

The proteins were collected in the liquid phase using a fraction collector and analyzed for molecular weight by MALDI-MS. In addition, part of the fraction was digested by trypsin or CNBR for identification by MALDI-MS and database searching. The protein profiles observed in FIG. 4 are clearly different between the AT1 and AT1E samples. A list of some of the more abundant proteins that have been identified by peptide mapping and MALDI-MS are listed in Table 2. There are several proteins in which expression is induced by estradiol, including PS2 estrogen-inducible protein, estradiol 17 β-dehydrogenase 7 and ERR1 estrogen receptor-like 1. Other proteins such as HSP 27 become much more highly expressed in response to estradiol. The change in protein expression between AT1 and AT1E is clearly evident as shown in FIGS. 2–4. In addition, the expression of key oncoproteins in AT1E starts to resemble those of the highly malignant cell line CaldCL1. This change in expression is evident in the online ESI-TOF-MS protein profile of FIG. 3 and also in the UV chromatogram protein profile. As expected the malignant and premalignant protein profiles vary markedly from the normal (immortalized) cell line MCF10A.

The use of nonporous separations with online ESI-MS detection in FIG. 3 clearly shows that the molecular weight of c-src in AT1E is 60,540 Da while that in CaldCL1 is 62,780 Da. The database value is 59,835 Da. Similar molecular weights were also determined by MALDI-MS for c-src. The two malignant cell lines, CaldCL1 and SUM-149, also show distinct differences in protein expression as seen in FIGS. 2 and 3. FIG. 5 shows a zoom-in 1-D image (from FIG. 3) comparing Cal dCL I and SLTM-149. The molecular weight of c-src in SUM-149 is 61,860 Da.

In order to study differences between c-src in the AT1 and AT1E cell lines, detailed analysis of the proteins collected in the liquid phase by the tandem column separation were performed using capillary LC-MS, CE-MS and MALDI-MS of the protein digests. The capillary LC-MS was performed using the LCT-MS and the IT-reTOF-MS. The CE-MS was performed on the IT-reTOFMS. The coverage of the c-src sequence was >50% using these methods with trypsin and CNBR digests. More than 45 peptides from c-src were detected and analyzed using these methods and as expected most of them are the same between AT1 and AT1E cell line. However, as shown in Table 2 for c-src, there are several peptides that are modified differently between AT1 and AT1E. It appears that there are differences in the phosphorylation patterns of the peptides detected. In addition, FIG. 2 shows changes in expression and molecular weight observed in HSP 27 as a function of cancer progression.

TABLE 2

A comparison of modified tryptic peptides between AT1 and AT1E

| Amino Acid | | Masses | | | Modifications | |
|---|---|---|---|---|---|---|
| start | end | Experimental | Database | Peptide sequence | AT1 | AT1E |
| 1 | 9 | 887.16 | 887.4951 | (−)MGSNKSKPK(D) | Acet N | Acet N, 2PO$_4$ |
| 10 | 14 | 655.96 | 656.2405 | (K)DASQR(R) | not modified | 1PO$_4$ |
| 156 | 159 | 545.24 | 545.3524 | (K)ITRR(E) | not modified | 1PO$_4$ |
| 159 | 163 | 756.50 | 756.6895 | (R)RESER(L) | not modified | 1PO$_4$ |
| 210 | 220 | 1215.52 | 1215.601 | (K)LDSGGFYITSR(T) | not modified | 1PO$_4$ |
| 244 | 260 | 1853.67 | 1854.0768 | (R)LTTVCPTSKPQTQGLAK(D) | not modified | 1PO$_4$ |
| 355 | 362 | 1082.95 | 1083.4277 | (K)GETGKYLR(L) | 2PO$_4$ | 1PO$_4$ |
| 363 | 382 | 2277.90 | 2276.5384 | (R)LPQLVDMAAQIASGMAYVER(M) | 1Met-ox | 2Met-ox, 1PO |
| 383 | 388 | 898.62 | 899.3599 | (R)MNYVHR(D) | 1PO$_4$ | 1Met-ox |
| 423 | 430 | 872.21 | 871.5042 | (R)QGAKFPIK(W) | pyroGlu | not modified |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method of producing protein profile maps, comprising:

a) providing:

i) a first sample comprising a plurality of proteins;

ii) a second sample comprising a plurality of proteins;

iii) a separating apparatus, wherein said separating apparatus separates proteins based on a physical property;

iv) a mass spectroscopy apparatus; and b) treating said first and second samples with said separating apparatus to produce a first separated protein sample and a second separated protein sample, wherein said first and second separated protein samples are collected from said separating apparatus in a plurality of fractions, each of said fractions defined by a physical property; and c) analyzing said plurality of fractions from each of said first and second separated protein samples with said mass spectroscopy apparatus to produce a protein profile map for each of said first and second samples, wherein said protein profile maps display protein abundance and mass of said first protein sample and said second protein sample, and wherein said protein profile maps displays each protein as a separate band corresponding to said mass of said first protein sample and said second protein sample, and wherein the intensity of said band corresponds to said protein abundance of said first protein sample and said second protein sample; and wherein said protein profile maps for each of said first and second samples are displayed side by side.

2. The method of claim 1, further comprising an automated sample handling device operably linked to said separating apparatus and said mass spectroscopy apparatus, wherein said sample handling device transfers said first and second samples to said separating apparatus, and wherein said sample handling device transfers said first and second separated protein samples from said separating apparatus to said mass spectroscopy apparatus.

3. The method of claim 2, further comprising a centralized control network operably linked to said automated sample handling device, said separating apparatus, and said mass spectroscopy apparatus, wherein said centralized control network controls the operations of said automated sample handling device, said separating apparatus, and said mass spectroscopy apparatus.

4. The method of claim 3, wherein said centralized control network comprises computer memory and a computer processor.

5. The method of claim 1, wherein said first sample comprises a cell lysate from a first cell type and said second sample comprises a cell lysate from second cell type.

6. The method of claim 5, wherein said first cell type is a cancerous cell type and said second cell type is a non-cancerous cell type.

7. The method of claim 1, wherein said bands are bands of different colors.

8. The method of claim 1, wherein said protein abundance and mass are indicative of the cell type of said protein sample.

9. The method of claim 1, further comprising the step of d) determining the identity of individual bands on said protein profile map.

10. The method of claim 6, further comprising the step of treating said first sample with an external agent prior to treating said first and second samples with said separating apparatus.

11. The method of claim 10, wherein said external agent comprises estradiol.

12. The method of claim 2, wherein said automated sample handling device comprises a switchable, multi-channel valve.

13. The method of claim 1, wherein said first and second samples further comprise a buffer, wherein said plurality of proteins are solubilized in said buffer and wherein said buffer is compatible with said separating apparatus and said mass spectroscopy apparatus.

14. The method of claim 13, wherein said buffer comprises a compound of the formula n-octyl $C_6$–$C_{12}$ glycopyranoside.

15. The method of claim 14, wherein said compound of the formula n-octyl $C_6$–$C_{12}$ glycopyranoside is selected from n-octyl β-D-glucopyranoside and n-octyl β-D-galactopyranoside.

16. The method of claim 1, wherein said separating apparatus comprises a liquid phase separating apparatus.

17. The method of claim 16, wherein said liquid phase separating apparatus comprises a reverse phase HPLC separating apparatus.

18. The method of claim 17, wherein said reverse phase HPLC comprises non-porous reverse phase HPLC.

19. The method of claim 1, wherein prior to said analyzing said first and second separated protein samples by mass spectroscopy, said first and second samples are divided into first and second portions and wherein said second portions are subjected to enzymatic digestion.

20. The method of claim 1, wherein said analyzing said first and second separated protein samples by mass spectrometry comprises analyzing said samples by electrospray ionization-orthogonal acceleration-time-of-flight mass spectrometry.

21. The method of claim 1, wherein said analyzing said first and second separated protein samples by mass spectrometry comprises analyzing said samples by a technique selected from the group consisting of ion trap mass spectrometry, ion trap/time-of-flight mass spectrometry, quadrupole and triple quadrupole mass spectrometry, Fourier Transform (ICR) mass spectrometry, and magnetic sector mass spectrometry.

22. A method of comparing protein profile maps, comprising:
a) providing:
i) a cell lysate derived from a cell of unknown type, said cell lysate comprising a plurality of proteins;
ii) a first protein profile map generated by the method of claim 1;
iii) a separating apparatus, wherein said separating apparatus separates proteins based on a physical property; and
iv) a mass spectroscopy apparatus; and
b) treating said cell lysate with said separating apparatus to produce a separated protein sample; wherein said separated protein sample is collected from said separating apparatus in a plurality of fractions, each of said fractions defined by a physical property;
c) analyzing said plurality of fractions from said separated protein sample with said mass spectroscopy apparatus to produce a second protein profile map, wherein said second protein profile maps displays each protein as a separate band corresponding to said mass of said first protein sample and said second protein sample, and wherein the intensity of said band corresponds to said protein abundance of said first protein sample and said second protein sample; and
d) comparing said first protein profile map and said second protein profile map, wherein said first and second protein profile maps are displayed side by side.

23. The method of claim 22, wherein said first protein profile map displays protein abundance and mass from cell lysates of several known cell types and said second protein profile map displays protein abundance and mass from said cell lysate of unknown type.

24. The method of claim 22, wherein said bands are bands of different colors.

25. The method of claim 23, wherein said protein abundance and mass are indicative of a cell identity.

26. A system for the production of a data representation of a protein profile map, comprising:
   a) a non-porous reverse phase HPLC separating apparatus;
   b) an automated sample handling apparatus configured to receive first and second separated protein samples from said reverse phase HPLC separating apparatus;
   c) a mass spectroscopy apparatus configured to receive proteins from said automated sample handling apparatus;
   d) a processor configured to produce a data representation of a protein profile map for said first and second separated protein samples analyzed by said mass spectroscopy apparatus, wherein said protein profile map displays protein abundance and mass of a separated protein sample, wherein said protein profile map displays proteins as separate bands corresponding to said protein abundance and mass of said separated protein sample, and wherein the intensity of said bands corresponds to the abundance of said proteins, wherein said protein profile maps for each of said first and second samples are displayed side by side; and
   e) a display apparatus that displays said protein profile maps.

27. The system of claim 26, wherein said protein profile map displays protein abundance as bands of varying intensity.

28. The system of claim 27, wherein said protein abundance is expressed as bands of different colors.

29. The system of claim 26, wherein said protein abundance and mass are indicative of a cell type of said protein sample.

30. The system of claim 26, wherein said processor is configured to determine the identity of individual bands on said protein profile map.

31. The system of claim 26, wherein said automated sample handling device comprises a switchable, multi-channel valve.

32. The system of claim 26, wherein said mass spectrometry apparatus comprises a electrospray ionization-orthogonal acceleration-time-of-flight mass spectrometry apparatus.

33. A method of producing protein profile maps, comprising:
   a) providing:
      i) a first sample comprising a plurality of proteins;
      ii) a second sample comprising a plurality of proteins;
      iii) a separating apparatus, wherein said separating apparatus separates proteins based on a physical property;
      iv) a mass spectroscopy apparatus; and
   b) treating said first and second samples with said separating apparatus to produce a first separated protein sample and a second separated protein sample, wherein said first and second separated protein samples are collected from said separating apparatus in a plurality of fractions, each of said fractions defined by a physical property;
   c) analyzing said plurality of fractions from each of said first and second separated protein samples with said mass spectroscopy apparatus to produce first and second protein profile maps for each of said first and second protein samples, wherein said protein profile maps display protein abundance and mass of said first protein sample and said second protein sample; and
   d) displaying a differential display protein map of said first and second protein profile maps, wherein said differential display protein map displays the difference in protein abundance versus mass between proteins in said first and second protein samples, and wherein said differential display protein profile map displays the difference in protein abundance between each protein as a separate band corresponding to said mass of said first protein sample and said second protein sample, and wherein the intensity of said band corresponds to the difference in protein abundance.

34. The method of claim 33, further comprising the step of displaying said first and second protein profile maps.

35. The method of claim 34, wherein said first and second protein profile maps and said differential display map are displayed side by side.

* * * * *

```
                           SEQUENCE LISTING

<160> NUMBER OF SEQ ID NOS: 10

<210> SEQ ID NO 1
<211> LENGTH: 10
<212> TYPE: PRT
<213> ORGANISM: artificial
<220> FEATURE:
<223> OTHER INFORMATION: synthetic

<400> SEQUENCE: 1

Met Gly Ser Asn Lys Ser Lys Pro Lys Asp
1               5                   10

<210> SEQ ID NO 2
<211> LENGTH: 7
<212> TYPE: PRT
<213> ORGANISM: artificial
<220> FEATURE:
<223> OTHER INFORMATION: synthetic

<400> SEQUENCE: 2

Lys Asp Ala Ser Gln Arg Arg
1               5

<210> SEQ ID NO 3
<211> LENGTH: 6
<212> TYPE: PRT
<213> ORGANISM: artificial
<220> FEATURE:
<223> OTHER INFORMATION: synthetic

<400> SEQUENCE: 3

Lys Ile Thr Arg Arg Glu
1               5

<210> SEQ ID NO 4
<211> LENGTH: 7
<212> TYPE: PRT
<213> ORGANISM: artificial
<220> FEATURE:
<223> OTHER INFORMATION: synthetic

<400> SEQUENCE: 4

Arg Arg Glu Ser Glu Arg Leu
1               5

<210> SEQ ID NO 5
<211> LENGTH: 13
<212> TYPE: PRT
<213> ORGANISM: artificial
<220> FEATURE:
<223> OTHER INFORMATION: synthetic

<400> SEQUENCE: 5

Lys Leu Asp Ser Gly Gly Phe Tyr Ile Thr Ser Arg Thr
1               5                   10
```

```
<210> SEQ ID NO 6
<211> LENGTH: 19
<212> TYPE: PRT
<213> ORGANISM: artificial
<220> FEATURE:
<223> OTHER INFORMATION: synthetic

<400> SEQUENCE: 6

Arg Leu Thr Thr Val Cys Pro Thr Ser Lys Pro Gln Thr Gln Gly Leu
1               5                   10                  15

Ala Lys Asp

<210> SEQ ID NO 7
<211> LENGTH: 10
<212> TYPE: PRT
<213> ORGANISM: artificial
<220> FEATURE:
<223> OTHER INFORMATION: synthetic

<400> SEQUENCE: 7

Lys Gly Glu Thr Gly Lys Tyr Leu Arg Leu
1               5                   10

<210> SEQ ID NO 8
<211> LENGTH: 22
<212> TYPE: PRT
<213> ORGANISM: artificial
<220> FEATURE:
<223> OTHER INFORMATION: synthetic

<400> SEQUENCE: 8

Arg Leu Pro Gln Leu Val Asp Met Ala Ala Gln Ile Ala Ser Gly Met
1               5                   10                  15

Ala Tyr Val Glu Arg Met
            20

<210> SEQ ID NO 9
<211> LENGTH: 8
<212> TYPE: PRT
<213> ORGANISM: artificial
<220> FEATURE:
<223> OTHER INFORMATION: synthetic

<400> SEQUENCE: 9

Arg Met Asn Tyr Val His Arg Asp
1               5

<210> SEQ ID NO 10
<211> LENGTH: 10
<212> TYPE: PRT
<213> ORGANISM: artificial
<220> FEATURE:
<223> OTHER INFORMATION: synthetic

<400> SEQUENCE: 10

Arg Gln Gly Ala Lys Phe Pro Ile Lys Trp
1               5                   10
```